United States Patent [19]
Ban et al.

[11] Patent Number: 5,624,961
[45] Date of Patent: Apr. 29, 1997

[54] BENZYLAMINOETHOXYBENZENE DERIVATIVES, PRODUCTION THEREOF AND USE THEREOF

[75] Inventors: Masakazu Ban; Kiyotaka Shinoda; Mitsuru Takahashi; Shuhei Deguchi; Hiroaki Taguchi; Takeo Katsushima, all of Ohtsu, Japan

[73] Assignee: Japan Tobacco Inc., Japan

[21] Appl. No.: 535,077

[22] PCT Filed: Feb. 10, 1995

[86] PCT No.: PCT/JP95/00187

§ 371 Date: Dec. 11, 1995

§ 102(e) Date: Dec. 11, 1995

[87] PCT Pub. No.: WO95/21811

PCT Pub. Date: Aug. 17, 1995

[30] Foreign Application Priority Data

Oct. 2, 1994 [JP] Japan ..................... 6-016694

[51] Int. Cl.$^6$ ............... C07C 217/18; C07C 217/58; C07C 213/02; A61K 31/135
[52] U.S. Cl. ............ 514/651; 514/539; 514/546; 514/618; 514/630; 560/42; 560/138; 564/158; 564/220; 564/354
[58] Field of Search ................ 564/354, 158, 564/220; 560/42, 138; 514/539, 546, 618, 630, 651

[56] References Cited

U.S. PATENT DOCUMENTS 4,818,772  4/1989  Pontagnier et al. ................ 514/651

FOREIGN PATENT DOCUMENTS 2-202857  8/1990  Japan .

OTHER PUBLICATIONS

Muramatsu et al., Eur. J. Pharmacol., vol. 300, pp. 155–157. 1996.

*Primary Examiner*—Richard L. Raymond
*Attorney, Agent, or Firm*—Leydig, Voit & Mayer, Ltd.

[57] ABSTRACT

Novel benzylaminoethoxybenzene derivatives of the formula (I)

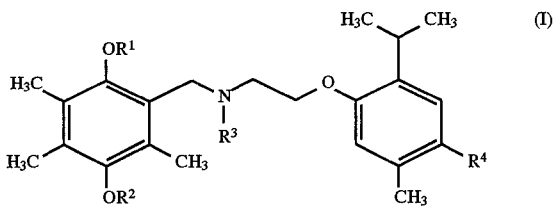

wherein $R^1$ is a hydrogen atom, a lower alkyl, a lower hydroxyalkyl, a lower alkoxyalkyl, an allyl or a benzyl; $R^2$ is a hydrogen atom, a lower alkyl, a lower acyl, an allyl or a benzyl; $R^3$ is a hydrogen atom, a lower alkyl, a lower alkoxyalkyl, a lower dialkylaminoalkyl or a lower acyl; and $R^4$ is a hydrogen atom, a halogen atom, a lower alkoxy, an amino, a lower acylamino, a hydroxy, a lower acyloxy, a lower acyl, a carboxy or a lower alkoxycarbonyl, salts thereof and solvates thereof. An $\alpha_1$-adrenoceptor blocker obtained from this compound has a strong $\alpha_1$-adrenoceptor blocking effect and causes less side effects such as orthostatic hypotension.

8 Claims, No Drawings

5,624,961

1

BENZYLAMINOETHOXYBENZENE DERIVATIVES, PRODUCTION THEREOF AND USE THEREOF

This application is a 371 of PCT/JP95/00187, filed Feb. 10, 1995.

TECHNICAL FIELD

The present invention relates to a novel benzylaminoethoxybenzene derivative which has a superior blocking effect on an α-adrenoceptor, particularly an $\alpha_1$-adrenoceptor and is useful for the prevention and treatment of diseases related to the sympathetic nervous system, such as hypertension, pulmonary hypertension, congestive heart failure, myocardial ischemia, arrhythmia, angina pectoris, peripheral vascular diseases, cardiovascular disorders due to the change in vascular resistance, abnormal serum lipid, benign prostrate hypertrophy, dysuria, diabetes, glaucoma, ocular hypertension, obesity, colic convulsion, gastrointestinal dyskinesia (e.g. irritable intestinal syndromes and constipation) and central nervous diseases (e.g. impotence, depression and senile dementia), a pharmaceutically acceptable salt thereof, a solvate thereof, a method for production thereof and a pharmaceutical composition comprising said compound.

BACKGROUND ART

There have been conventionally investigated and developed blockers of various $\alpha_1$-adrenoceptors, and many compounds have been reported. As the compounds having an $\alpha_1$-adrenoceptor-blocking effect, for example, Arzneim. Forsch., vol. 17, 305 (1967) discloses moxisylyte hydrochloride, which is not entirely satisfactory in the effect as an $\alpha_1$-adrenoceptor blocker. Also, prazosin hydrochloride is used as a therapeutic agent for hypertension and dysuria, whereas it causes side effects such as orthostatic hypotension.

The conventional $\alpha_1$-adrenoceptor blockers are not sufficient for the treatment of the diseases mediated by the sympathetic nervous system, such as hypertension, pulmonary hypertension, congestive heart failure, myocardial ischemia, arrhythmia, angina pectoris, peripheral vascular diseases, cardiovascular disorders due to the change in vascular resistance, abnormal serum lipid, benign prostatic hypertrophy, dysuria, diabetes, glaucoma, ocular hypertension, obesity, colic convulsion, gastrointestinal dyskinesia (e.g. irritable intestinal syndromes and constipation) and central nervous diseases (e.g. impotence, depression and senile demantia). In addition, the conventional $\alpha_1$-adrenoceptor blockers are known to cause side effects such as orthostatic hypotension. It is therefore an object of the present invention to overcome these defects of the conventional $\alpha_1$-adrenoceptor blockers and provide an $\alpha_1$-adrenoceptor blocker which exhibits strong $\alpha_1$-adrenoceptor-blocking effect and causes less side effects such as orthostatic hypotension.

DISCLOSURE OF THE INVENTION

The present inventors have synthesized various compounds in an attempt to obtain a medicine having superior $\alpha_1$-adrenoceptor blocking action on the symptoms mediated by the sympathetic nervous system, such as hypertension, pulmonary hypertension, congestive heart failure, myocardial ischemia, arrhythmia, angina pectoris, peripheral vascular diseases, cardiovascular disorders due to the change in vascular resistance, abnormal serum lipid, benign prostatic hypertrophy, dysuria, diabetes, glaucoma, ocular

2 hypertension, obesity, colic convulsion, gastrointestinal dyskinesia (e.g. irritable intestinal syndromes and constipation) and central nervous diseases (e.g. impotence, depression and senile demantia), and studied their pharmacological actions. As a result, they have found that a specific, novel benzylaminoethoxybenzene derivative is superior in $\alpha_1$-adrenoceptor-blocking effect and that it causes less side effects such as orthostatic hypotension, and completed the invention.

Accordingly, the present invention relates to novel benzylaminoethoxybenzene derivatives of the formula (I)

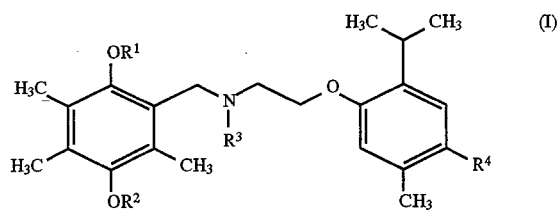

wherein
$R^1$ is a hydrogen atom, a lower alkyl, a lower hydroxyalkyl, a lower alkoxyalkyl, an allyl or a benzyl;
$R^2$ is a hydrogen atom, a lower alkyl, a lower acyl, an allyl or a benzyl;
$R^3$ is a hydrogen atom, a lower alkyl, a lower alkoxyalkyl, a lower dialkylaminoalkyl or a lower acyl; and
$R^4$ is a hydrogen atom, a halogen atom, a lower alkoxy, an amino, a lower acylamino, a hydroxy, a lower acyloxy, a lower acyl, a carboxy or a lower alkoxycarbonyl,
salts thereof and solvates thereof.

The present invention also relates to pharmaceutical compositions containing said compounds, and to the production of said compounds.

In particular, the present invention relates to benzylaminoethoxybenzene derivatives of the formula (I')

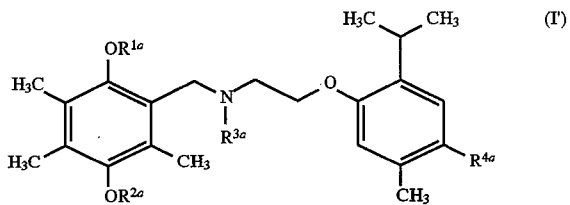

wherein
$R^{1a}$ is a hydrogen atom, a lower alkyl, a lower hydroxyalkyl or a lower alkoxyalkyl;
$R^{2a}$ is a hydrogen atom or a lower acyl;
$R^{3a}$ is a hydrogen atom, a lower alkyl or a lower alkoxyalkyl; and
$R^{4a}$ is a hydroxy or a lower acyloxy,
salts thereof and solvates thereof.

In the present specification, each symbol denotes the following.

The lower alkyl means a straight or branched hydrocarbon having 1 to 4 carbon atoms. Examples thereof include methyl, ethyl, propyl, isopropyl, butyl, isobutyl, sec-butyl and tertbutyl, with preference given to methyl and ethyl.

The lower alkoxy is a group wherein the hydrogen atom of hydroxy (—OH) is substituted by the aforementioned lower alkyl, and is exemplified by methoxy, ethoxy, propoxy, isopropoxy, butoxy, isobutoxy, sec-butoxy and tert-butoxy, with preference given to methoxy.

The lower hydroxyalkyl is a straight or branched hydroxyalkyl having 2 to 4 carbon atoms, and is exemplified by 2-hydroxyethyl, 2-hydroxypropyl, 3-hydroxypropyl, 2-hydroxy-1-methylethyl, 2-hydroxybutyl, 3-hydroxybutyl, 4-hydroxybutyl, 1,1-dimethyl-2-hydroxyethyl, 2-hydroxy-1-methylpropyl, 2-hydroxy-2-methylpropyl, 3-hydroxy-1-methylpropyl and 3-hydroxy-2-methylpropyl, with preference given to 2-hydroxyethyl.

The lower alkoxyalkyl is a group wherein the hydrogen atom of hydroxy (—OH) of the aforementioned lower hydroxyalkyl is substituted by methyl or ethyl, and is exemplified by 2-methoxyethyl, 2-methoxypropyl, 3-methoxypropyl, 2-methoxy-1-methylethyl, 2-methoxybutyl, 3-methoxybutyl, 4-methoxybutyl, 1,1-dimethyl-2-methoxyethyl, 2-methoxy-1-methylpropyl, 2-methoxy-2-methylpropyl, 3-methoxy-1-methylpropyl, 3-methoxy-2-methylpropyl, 2-ethoxyethyl, 2-ethoxypropyl, 3-ethoxypropyl, 2-ethoxy-1-methylethyl, 2-ethoxybutyl, 3-ethoxybutyl, 4-ethoxybutyl, 1,1-dimethyl-2-ethoxyethyl, 2-ethoxy-1-methylpropyl, 2-ethoxy-2-methylpropyl, 3-ethoxy-1-methylpropyl and 3-ethoxy-2-methylpropyl, with preference given to 2-methoxyethyl.

The lower acyl means formyl (—CHO) or a group wherein the hydrogen atom of formyl is substituted by the aforementioned lower alkyl, and is preferably acetyl.

The lower acyloxy is a group wherein the hydrogen atom of hydroxy (—OH) is substituted by the aforementioned lower acyl, and is preferably acetoxy.

The lower dialkylaminoalkyl is a group wherein hydroxy (—OH) of the aforementioned lower hydroxyalkyl is substituted by dimethylamino or diethylamino, and is preferably 2-diethylaminoethyl.

The halogen atom is, for example, fluorine atom, chlorine atom, bromine atom or iodine atom, with preference given to chlorine atom.

The lower acylamino is a group wherein one of the hydrogen atoms of amino (—NH$_2$) is substituted by the aforementioned lower acyl, and is preferably acetylamino.

The lower alkoxycarbonyl is a group wherein the hydrogen atom of carboxy (—COOH) is substituted by the aforementioned lower alkyl, and is preferably methoxycarbonyl.

The novel compound of the present invention encompasses compounds having asymmetric carbon, depending on the kind of substituents. Accordingly, the novel compound of the present invention encompasses mixtures of various optical isomers and isolated isomers. The novel compound of the formula (I) of the present invention may be in the form of a salt such as an acid addition salt, particularly a pharmaceutically acceptable non-toxic acid addition salt. Depending on the kind of substituents, the compound can be in the form of a salt with base, particularly a pharmaceutically acceptable non-toxic base addition salt.

Examples of such salt include addition salts with acid such as mineral acid (e.g. hydrochloric acid, hydrobromic acid, hydroiodic acid, sulfuric acid, nitric acid and phosphoric acid), organic acid (e.g. formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid and p-toluenesulfonic acid) and acidic amino acid (e.g. aspartic acid and glutamic acid); addition salts with base such as inorganic base (e.g. sodium, potassium, magnesium, calcium and aluminum) and organic base (e.g. methylamine, ethylamine and ethanolamine); salts with basic amino acid such as lysine and ornithine; and ammonium salt. The salt of the novel compound of the present invention may be in the form of a solvate. Examples of the solvent include water, methanol, ethanol, propanol and isopropyl alcohol.

Specific examples of the compound of the present invention include N-(3-hydroxy-6-methoxy-2,4,5-trimethylbenzyl)-N-methyl-2-(4-hydroxy-2-isopropyl-5-methylphenoxy)ethylamine, N-{3-hydroxy-6-(2-hydroxyethoxy)-2,4,5-trimethylbenzyl}-N-methyl-2-(4-hydroxy-2-isopropyl-5-methylphenoxy)ethylamine, N-(3-hydroxy-6-methoxy-2,4,5-trimethylbenzyl)-2-(4-acetylamino-2-isopropyl-5-methylphenoxy)ethylamine, N-(2-ethoxy-5-hydroxy-3,4,6-trimethylbenzyl)-N-methyl-2-(4-hydroxy-2-isopropyl-5-methylphenoxy)ethylamine, N-(3-acetoxy-6-ethoxy-2,4,5-trimethylbenzyl)-N-methyl-2-(4-acetoxy-2-isopropyl-5-methylphenoxy)ethylamine, N-(2-diethylaminoethyl)-N-(3-hydroxy-6-methoxy-2,4,5-trimethylbenzyl)-2-(2-isopropyl-5-methylphenoxy) ethylamine, N-ethyl-N-(3-hydroxy-6-methoxy-2,4,5-trimethylbenzyl)-2-(4-chloro-2-isopropyl-5-methylphenoxy)ethylamine, N-{2-(2-isopropyl-5-methylphenoxy)ethyl}-N-(2,5-dimethoxy-3,4,6-trimethylbenzyl)acetamide, N-(3-hydroxy-6-methoxy-2,4,5-trimethylbenzyl)-N-methyl-2-(4-acetyl-2-isopropyl-5-methylphenoxy)ethylamine, N-(2,5-dimethoxy-3,4,6-trimethylbenzyl)-N-methyl-2-( 4-acetylamino-2-isopropyl-5-methylphenoxy)ethylamine, N-(2,5-dimethoxy-3,4,6-trimethylbenzyl)-N-methyl-2-(4-amino-2-isopropyl-5-methylphenoxy)ethylamine, N-(3-hydroxy-6-methoxy-2,4,5-trimethylbenzyl)-N-methyl-2-(2-isopropyl-5-methylphenoxy)ethylamine, N-(3-benzyloxy-6-methoxy-2,4,5-trimethylbenzyl)-N-methyl-2-(2-isopropyl-5-methylphenoxy)ethylamine, N-(3-isopropoxy-6-methoxy-2,4,5-trimethylbenzyl)-N-methyl-2-(2-isopropyl-5-methylphenoxy)ethylamine, N-(3-ethoxy-6-methoxy-2,4,5-trimethylbenzyl)-N-methyl-2-(2-isopropyl-5-methylphenoxy)ethylamine, N-{3-hydroxy-6-(2-hydroxyethoxy)-2,4,5-trimethylbenzyl}-N-methyl-2-(2-isopropyl-5-methylphenoxy)ethylamine, N-{3-acetoxy-6-(2-propenyloxy)-2,4,5-trimethylbenzyl}-N-methyl-2-(2-isopropyl-5-methylphenoxy)ethylamine, N-(3-acetoxy-6-isopropoxy-2,4,5-trimethylbenzyl)-N-ethyl-2-(4-chloro-2-isopropyl-5-methylphenoxy)ethylamine, N-(3-ethoxy-6-hydroxy-2,4,5-trimethylbenzyl)-2-(2-isopropyl-5-methylphenoxy)ethylamine, N-(2-benzyloxy-5-ethoxy-3,4,6-trimethylbenzyl)-2-(2-isopropyl-5-methylphenoxy) ethylamine, N-(3-hydroxy-6-methoxy-2,4,5-trimethylbenzyl)-2-(4-hydroxy-2-isopropyl-5-methylphenoxy)ethylamine, N-(3-hydroxy-6-methoxy-2,4,5-trimethylbenzyl)-N-isopropyl-2-(4-hydroxy-2-isopropyl-5-methylphenoxy)ethylamine, N-(3-hydroxy-6-methoxy-2,4,5-trimethylbenzyl)-N-(2-methoxyethyl)-2-(4-hydroxy-2-isopropyl-5-methylphenoxy)ethylamine, N-(3-hydroxy-6-propoxy-2,4,5-trimethylbenzyl)-N-methyl-2-(4-hydroxy-2-isopropyl-5-methylphenoxy)ethylamine, N-tert-butyl-N-(3-hydroxy-6-methoxy-2,4,5-trimethylbenzyl)-2-(4-hydroxy-2-isopropyl-5-methylphenoxy)ethylamine, N-(2-butoxy-5-hydroxy-3,4,6-trimethylbenzyl)-N-methyl-2-(4-hydroxy-2-isopropyl-5-methylphenoxy)ethylamine, N-(3-acetoxy-6-hydroxy-2,4,5-trimethylbenzyl)-N-methyl-2-(4-hydroxy-2-isopropyl-5-methylphenoxy)ethylamine, N-(2,5-dimethoxy-3,4,6-trimethylbenzyl)-N-methyl-2-(4-hydroxy-2-isopropyl-5-methylphenoxy)ethylamine, N-{3-hydroxy-6-(2-methoxyethoxy)-2,4,5-trimethylbenzyl}-N-methyl-2-(4-hydroxy-2-isopropyl-5-methylphenoxy)ethylamine, N-(2-ethoxy-5-hydroxy-3,4,6-trimethylbenzyl)-N-isopropyl-2-(4-hydroxy-2-isopropyl-5-methylphenoxy)ethylamine, N-ethyl-N-(3-hydroxy-6-methoxy-2,4,5-trimethylbenzyl)-2-(4-hydroxy-2-isopropyl-5-methylphenoxy)ethylamine and N-(2,5-dimethoxy-3,4,6-trimethylbenzyl)-N-methyl-2-(2-isopropyl-4-methoxy-5-methylphenoxy)ethylamine.

Production method

The novel compound and salt thereof of the present invention can be produced by various synthesis methods, according to the characteristics based on the basic skeleton of the compound or the kind of substituents. Typical methods for production are exemplified in the following.

Production 1

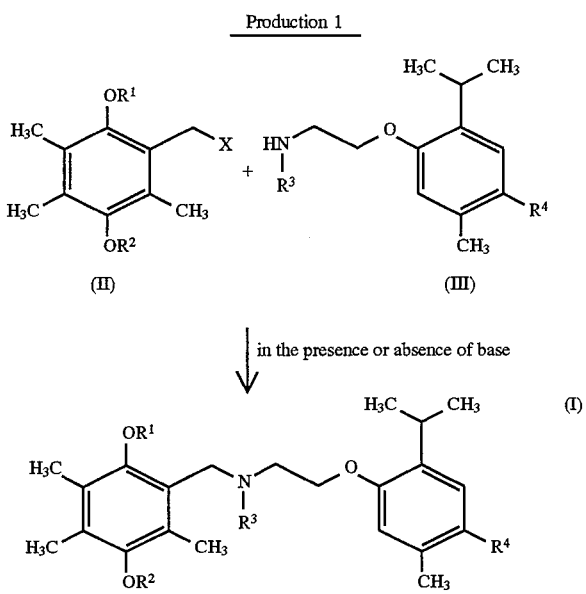

wherein $R^1$ is hydrogen atom, a lower alkyl, a lower hydroxyalkyl, a lower alkoxyalkyl, allyl or benzyl; $R^2$ is hydrogen atom, a lower alkyl, a lower acyl, allyl or benzyl; $R^3$ is hydrogen atom, a lower alkyl, a lower alkoxyalkyl, a lower dialkylaminoalkyl or a lower acyl; $R^4$ is hydrogen atom, a halogen atom, a lower alkoxy, amino, a lower acylamino, hydroxy, a lower acyloxy, a lower acyl, carboxy or a lower alkoxycarbonyl; and X is a halogen atom, an alkylsulfonyloxy having 1 to 4 carbon atoms or arylsulfonyloxy having 6 to 10 carbon atoms.

The Production 1 as exemplified comprises reacting a compound of the formula (II) and a compound of the formula (III) or an acid addition salt thereof in a suitable solvent or without solvent in the presence or absence of a base, whereby the novel compound of the formula (I) of the present invention is obtained. These free compounds are converted to pharmaceutically acceptable salts or solvates thereof on demand by the addition of a suitable organic or inorganic acid or base.

Of the compounds of the formula (I) thus produced, a compound wherein at least one of $R^1$, $R^2$ and $R^3$ is lower acyl and a compound wherein $R^4$ is lower acyloxy, lower acylamino or lower alkoxycarbonyl can be converted to a compound wherein the at least one of $R^1$, $R^2$ and $R^3$ is hydrogen atom and a compound wherein $R^4$ is hydroxy, amino or carboxy, respectively, by a conventional method.

A compound wherein at least one of $R^1$, $R^2$ and $R^3$ is hydrogen atom and a compound wherein $R^4$ is hydroxy, amino or carboxy can be converted to a compound wherein the at least one of $R^1$, $R^2$ and $R^3$ is lower acyl, benzyl or lower alkyl and a compound wherein $R^4$ is lower acyloxy, lower acylamino or lower alkoxycarbonyl, respectively, by a conventional method such as acylation, alkylation or esterification.

When desired, these free compounds are converted to pharmaceutically acceptable salts or solvates thereof by the addition of a suitable organic or inorganic acid or base.

Examples of the reaction solvent include alcohols such as methanol, ethanol, propanol and isopropyl alcohol; hydrocarbons such as benzene, toluene and xylene; halogenated hydrocarbons such as methylene chloride, chloroform, carbon tetrachloride and 1,2-dichloroethane; ethers such as tetrahydrofuran, dioxane and diethyl ether; acetonitrile; N,N-dimethylformamide (DMF); dimethyl sulfoxide; and ethyl acetate, which are inert to the reaction and used as appropriate. The reaction can be also carried out without solvent.

When the reaction proceeds in the presence of a base, it is preferable that an organic base such as triethylamine and pyridine, inorganic base such as sodium carbonate, potassium carbonate and sodium hydride, or n-butyllithium be used. When the base is a liquid at the reaction temperature, the base may be used as a solvent.

While these reactions proceed from under cooling to under heating, they are generally carried out under heating (under reflux) to promote the reaction. Preferably, the reaction is carried out at a temperature from room temperature to under heating (under reflux).

Production 2

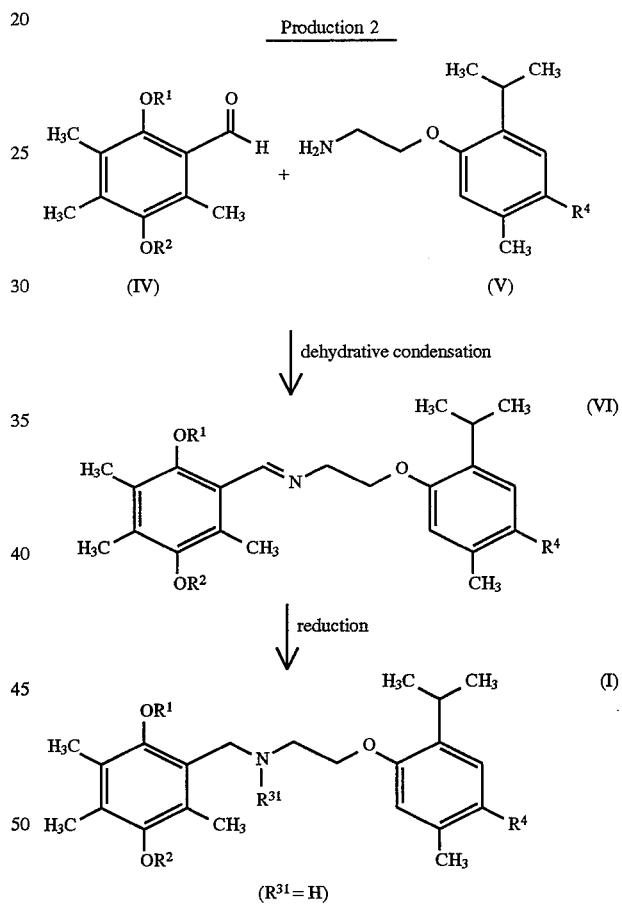

wherein $R^1$ is hydrogen atom, a lower alkyl, a lower hydroxyalkyl, a lower alkoxyalkyl, allyl or benzyl; $R^2$ is hydrogen atom, a lower alkyl, a lower acyl, allyl or benzyl; $R^{31}$ is hydrogen atom; and $R^4$ is hydrogen atom, a halogen atom, a lower alkoxy, amino, a lower acylamino, hydroxy, a lower acyloxy, a lower acyl, carboxy or a lower alkoxycarbonyl.

The Production 2 as exemplified comprises dehydrative condensation of a compound of the formula (IV) and a compound of the formula (V) in the presence or absence of an acid catalyst to produce a benzylidenealkylamine derivative of the formula (VI) as an intermediate for synthesis, followed by reduction, which is known as reductive amination, whereby the novel compound of the formula (I)

of the present invention is obtained. These free compounds are converted to pharmaceutically acceptable salts or solvates thereof on demand by the addition of a suitable organic or inorganic acid or base.

Of the compounds of the formula (I) thus produced, a compound wherein at least one of $R^1$ and $R^2$ is lower acyl and a compound wherein $R^4$ is lower acyloxy, lower acylamino or lower alkoxycarbonyl can be converted to a compound wherein the at least one of $R^1$ and $R^2$ is hydrogen atom and a compound wherein $R^4$ is hydroxy, amino or carboxy, respectively, by a conventional method.

A compound (I) wherein at least one of $R^1$, $R^2$ and $R^3$ is hydrogen atom and a compound (I) wherein $R^4$ is hydroxy, amino or carboxy can be converted to a compound (I) wherein the at least one of $R^1$, $R^2$ and $R^3$ is lower acyl or lower alkyl and a compound (I) wherein $R^4$ is lower acyloxy, lower acylamino or lower alkoxycarbonyl, respectively, by a conventional method such as acylation, alkylation or esterification.

When desired, these free compounds are converted to pharmaceutically acceptable salts or solvates thereof on demand by the addition of a suitable organic or inorganic acid or base.

The dehydrative condensation can be carried out in a solvent such as alcohols (e.g. methanol, ethanol, propanol and isopropyl alcohol); ethers (e.g. diethyl ether, tetrahydrofuran and dioxane); hydrocarbons (e.g. benzene, toluene and xylene); and halogenated hydrocarbons (e.g. methylene chloride, carbon tetrachloride, 1,2-dichloroethane and chloroform).

Organic acids such as p-toluenesulfonic acid and inorganic acids such as boron trifluoride can be used as an acid catalyst.

While these reactions proceed from under cooling to under heating, they are generally carried out under heating (under reflux) to promote the reaction, with preference given to a temperature from room temperature to under heating (under reflux). The reaction can be carried out while dehydrating by the use of an azeotropic dehydrator or molecular seive.

The reduction can be carried out in the same solvent as in the aforementioned dehydrative condensation.

In Production 2, a benzylidenealkylamine derivative of the formula (VI), which is an intermediate dehydratively condensed compound for the compound of the present invention, may be isolated and reduced, or the two reactions of dehydrative condensation and reduction may be continuously or simultaneously carried out. Examples of the reducing agent include sodium borohydride and sodium cyanoborohydride. A catalytic hydrogenation may be carried out in the presence of a catalyst such as palladium carbon and platinum oxide under normal pressure or under pressurization. The reduction is preferably carried out from 0° C. to under heating (under reflux).

The level of the blocking effect on $\alpha_1$-adrenoceptor and orthostatic hypotensive effect of the novel compound of the present invention was investigated as in the following.

EXPERIMENTAL EXAMPLE 1

Blocking of $\alpha_1$-adrenoceptor
(1) Test method

The $\alpha_1$-adrenoceptor blocking effect was determined using a preparation from the thoracic aorta of rabbit, according to the Magnus method and expressed as $pA_2$ value. The $pA_2$ values of the compound of the present invention and the aforementioned moxisylyte hydrochloride and prazosin hydrochloride used as control compounds are shown in Table 1.

(2) Test results

TABLE 1

($pA_2$ value determination results)

| Compound | $pA_2$ value | Compound | $pA_2$ value |
| --- | --- | --- | --- |
| Compound of Ex. 1 | 9.0 | Compound of Ex. 17 | 7.4 |
| Compound of Ex. 2 | 8.1 | Compound of Ex. 18 | 7.2 |
| Compound of Ex. 3 | 8.2 | Compound of Ex. 19 | 7.3 |
| Compound of Ex. 4 | 8.5 | Compound of Ex. 20 | 7.2 |
| Compound of Ex. 5 | 8.3 | Compound of Ex. 21 | 9.8 |
| Compound of Ex. 6 | 7.5 | Compound of Ex. 22 | 7.5 |
| Compound of Ex. 7 | 7.7 | Compound of Ex. 23 | 7.6 |
| Compound of Ex. 8 | 7.3 | Compound of Ex. 24 | 8.3 |
| Compound of Ex. 9 | 7.5 | Compound of Ex. 26 | 8.3 |
| Compound of Ex. 10 | 7.4 | Compound of Ex. 27 | 8.1 |
| Compound of Ex. 11 | 8.3 | Compound of Ex. 28 | 9.0 |
| Compound of Ex. 12 | 8.1 | Compound of Ex. 29 | 8.2 |
| Compound of Ex. 14 | 7.6 | Compound of Ex. 30 | 7.2 |
| Compound of Ex. 15 | 7.5 | Compound of Ex. 31 | 8.6 |
| Compound of Ex. 16 | 7.6 | Compound of Ex. 32 | 7.2 |
| prazosin hydrochloride | 8.6 | moxisylyte hydrochloride | 7.6 |

The results reveal that the compounds of the present invention exhibited markedly strong blocking effect on $\alpha_1$-adrenoceptor. Some of them showed markedly strong blocking effect in comparison to the control compounds, moxisylyte hydrochloride and prazosin hydrochloride.

EXPERIMENTAL EXAMPLE 2

Orthostatic hypotensive effect
(1) Test method

The orthostatic hypotensive effect was examined by the following method which is in accordance with the method of Journal of Pharmacological Methods, vol. 5, p. 53 (1981). A rabbit was fixed at the dorsal position without anesthetization on an orthostatic hypotension measurement apparatus. Polyethylene catheters were inserted in right femoral artery and right femoral vein, and the catheter inserted in the artery was connected to a pressure transducer. The head of the rabbit was tilted rapidly at an angle of 90° from the horizontal position at 15 min intervals with the heart position as a rotational axis, and brought back to the horizontal position one minute later. The tilting was repeated three times, and after confirmation of occurrence of a constant response, a drug was administered from the polyethylene catheter inserted in the vein. The level of orthostatic hypotension caused by the drug was evaluated according to the orthostatic index (O.I.) calculated from the following formula and compared by the dose of the compound at which the O.I. value shows 90%. The results are shown in Table 2.

Orthostatic Response (O.R.) = (blood pressure immediately before termination of tilting)/(blood pressure immediately before beginning of tilting)

O.I. (%) = (O.R. after drug administration/O.R. before drug administration) × 100

(2) Test results

TABLE 2

(level of orthostatic hypotension)

| Compound | Dose necessary for O.I. value to achieve 90% (μg/kg, iv) |
| --- | --- |
| Compound of Ex. 1 | 56.4 |
| Compound of Ex. 4 | 61.3 |
| Compound of Ex. 21 | 32.8 |
| Compound of Ex. 28 | 40.3 |
| prazosin hydrochloride | 5.6 |

The results reveal that the compound of the present invention showed $pA_2$ value, which is the index of $\alpha_1$-adrenoceptor blocking effect, indicating the activity equal to blocking effect, indicating the activity equal to or higher than the activity of the control compound, prazosin hydrochloride, while the dose corresponding to the same O.I. value was greater. Accordingly, it was confirmed that the compound of the present invention does not easily cause orthostatic hypotension.

Based on the above results, it is evident that the compound of the present invention has a superior $\alpha_1$-adrenoceptor blocking effect and a weak orthostatic hypotensive effect.

Pharmaceutical compositions containing one or more of the compound of the formula (I), a pharmaceutically acceptable salt thereof or a solvate thereof can be prepared by admixing the compound with carriers, excipients and other additives conventionally used for manufacturing pharmaceuticals. The include, for example, solid or liquid non-toxic substances for pharmaceuticals. Examples thereof include lactose, magnesium stearate, starch, talc, gelatin, agar, pectin, gum arabic, olive oil, sesami oil, cacao butter and ethylene glycol, and other conventional ones.

Administration route may be oral using tablet, pill, capsule, granule, powder, liquid and the like, or parenteral using injection (intravenous, intramuscular), suppository, transdermal agent and the like. While the dose varies depending on symptom, age, sex etc. of administration targets and is determined in close accordance with the condition of individual, it is generally 0.1–1,000 mg, preferably 1–500 mg for an adult per day in the case of oral administration, which is administered in a single to 2–4 times divided doses.

The present invention is described in more detail by illustrative Examples in the following. It should be understood that the invention is not limited to these Examples.

Example 1

Synthesis of N-(3-hydroxy-6-methoxy-2,4,5-trimethylbenzyl)-N-methyl- 2-(4-hydroxy-2-isopropyl-5-methylphenoxy)ethylamine ½ fumarate Triethylamine (2.8 ml) was added dropwise to a solution of N-methyl-2-(4-hydroxy-2-isopropyl-5-methylphenoxy)ethylamine hydrochloride (2.60 g) and 3-hydroxy-6-methoxy-2,4,5-trimethylbenzyl chloride (2.15 g) in N,N-dimethylformamide (20 ml), and the mixture was stirred at room temperature for 16 hours. After the completion of the reaction, the reaction mixture was poured on ice water and extracted with ethyl acetate. The extract was washed with water, dried and concentrated to give 3.5 g of a pale brown oil. The oil was dissolved in a small amount of tetrahydrofuran and fumaric acid (0.5 g) was added. The mixture was heated for dissolution. The solvent was distilled off under reduced pressure and the residue was recrystallized from a mixed solvent of tetrahydrofuran-ethyl acetate to give 3.2 g of the title compound (colorless crystals).

Melting point: 173.9°–175.0° C.

IR(KBr) cm$^{-1}$: 3400, 2980, 2740, 1620, 1580, 1515, 1470, 1425, 1380, 1365, 1265, 1210, 1135, 1090, 1070, 1020, 980, 885, 830, 670

NMR(DMSO-d$_6$) δ: 6.60(2H, s), 6.59(1H, s), 3.93(2H, t), 3.56(2H, s), 3.54(3H, s), 3.13(1H, m), 2.75(2H, t), 2.21(3H, s), 2.19(3H, s), 2.09(3H,s), 2.08(3H,s), 2.05(3H,s),1.07(6H, d)

Elemental analysis ($C_{24}H_{35}NO_4 \cdot \frac{1}{2}C_4H_4O_4$) Calculated: C, 67.95; H, 8.11; N, 3.05 Found: C, 67.69; H, 8.32; N, 2.88

In the same manner, monofumarate was produced.

Melting point: 92°–106° C.

Elemental analysis ($C_{24}H_{35}NO_4 \cdot C_4H_4O_4 \cdot 2H_2O$) Calculated: C, 60.74; H, 7.83; N, 2.53 Found: C, 60.89; H,7.70; N,2.50

In the same manner, sulfate was produced.

Melting point: 205°–210° C.

Elemental analysis ($C_{24}H_{35}NO_4 \cdot H_2SO_4$) Calculated: C,57.70; H,7.46; N,2.80; S,6.42 Found: C,57.52; H,7.34; N,2.81; S,6.40

In the same manner, maleate was produced.

Melting point: gradually decomposed from 118° C.

Elemental analysis ($C_{24}H_{35}NO_4 \cdot C_4H_4O_4 \cdot \frac{1}{2}H_2O$) Calculated: C,63.86; H,7.66; N,2.66 Found: C,63.97; H,7.68; N,2.76

In the same manner, phosphate was produced.

Melting point: 139°–144° C.

Elemental analysis ($C_{24}H_{35}NO_4 \cdot H_3PO_4 \cdot 2H_2O$) Calculated: C,53.82; H,7.90; N,2.62; P,5.78 Found: C,53.44; H,7.72; N,2.63; P,5.59

In the same manner, oxalate was produced.

Melting point: 157°–163° C.

Elemental analysis ($C_{24}H_{35}NO_4 \cdot C_2H_2O_4$) Calculated: C,63.53; H,7.59; N,2.81 Found: C,63.28; H,7.55; N,2.85

Example 2

Synthesis of N-{3-hydroxy-6-(2-hydroxyethoxy)-2,4,5-trimethylbenzyl}-N-methyl-2-(4-hydroxy-2-isopropyl-5-methylphenoxy)ethylamine hydrochloride Triethylamine (2.8 ml) was added dropwise to a solution of N-methyl-2-(4-hydroxy-2-isopropyl-5-methylphenoxy) ethylamine hydrochloride (2.60 g) and 3-hydroxy-6-(2-hydroxyethoxy)-2,4,5-trimethylbenzyl chloride (2.45 g) in N,N-dimethylformamide (20 ml), and the mixture was stirred at room temperature for 16 hours. After the completion of the reaction, the reaction mixture was poured on ice water and extracted with ethyl acetate. The extract was washed with water, dried and concentrated to give 3.8 g of a pale brown oil. The oil was dissolved in a small amount of methanol and conc. hydrochloric acid (1.2 ml) was added. The solvent was distilled off under reduced pressure and the residue was recrystallized from ethanol-diethyl ether to give 2.9 g of the title compound (colorless crystals).

Melting point: gradually decomposed from 110° C.

IR(KBr) cm$^{-1}$: 3300, 2980, 1620, 1510, 1460, 1415, 1385, 1295, 1270, 1210, 1150, 1085, 1040, 890, 820, 675

NMR(DMSO-d$_6$) δ: 9.42(1H,brs), 8.83(1H,s), 8.25(1H, s), 6.71 (1H,s), 6.69(1H,s), 5.44(1H,brs), 4.51 (2H,m), 4.31

(2H,brs), 3.74(2H,m), 3.65(2H,brs), 3.39(2H,brs), 3.18(1H, m), 2.82(3H,d), 2.27(3H,s), 2.15(3H,s), 2.14(3H,s), 2.08 (3H,s), 1.09 (6H,m)

Elemental analysis ($C_{25}H_{37}NO_5 \cdot HCl \cdot 5/4H_2O$) Calculated: C,61.22; H,8.32; N,2.86; Cl,7.23 Found: C,61.23; H,8.22; N,2.78; Cl,7.24

Example 3

Synthesis of N-(3-hydroxy-6-methoxy-2,4,5-trimethylbenzyl)-2-(4-acetylamino-2-isopropyl-5-methylphenoxy)ethylamine 2-(4-Acetylamino-2-isopropyl-5-methylphenoxy) ethylamine (1.0 g) and triethylamine (0.50 g) were dissolved in N,N-dimethylformamide (20 ml), and 3-hydroxy-6-methoxy-2,4,5-trimethylbenzyl chloride (0.86 g) dissolved in N,N-dimethylformamide (10 ml) was added dropwise while stirring the mixture at room temperature. The mixture was stirred for 5 hours. After the completion of the reaction, the solvent was distilled off, and water and ethyl acetate were added. The mixture was stirred and an insoluble matter was collected by filtration. The obtained solid was recrystallized from ethyl acetate to give 100 mg of the title compound.

Melting point: gradually decomposed from 75° C.

IR(KBr) $cm^{-1}$: 3410, 3300, 2970, 1660, 1515, 1460, 1410, 1350, 1255, 1215, 1090, 1015, 890

NMR(DMSO-$d_6$) δ: 9.14(1H,s), 7.76(1H,s), 7.01 (1H,s), 6.75(1H,s), 4.00(2H,t), 3.72(2H,s), 3.59(3H,s), 3.15(1H,m), 2.92(2H,t), 2.16(3H,s), 2.10(3H,s), 2.08(3H,s), 2.07(3H,s), 1.99(3H,s), 1.09(6H,d)

Elemental analysis ($C_{25}H_{36}N_2O_4 \cdot 2H_2O$) Calculated: C,65.91; H,8.63; N,6.15 Found: C,65.54; H,8.33; N,6.12

Example 4

Synthesis of N-(2-ethoxy-5-hydroxy-3,4,6-trimethylbenzyl)-N-methyl-2-(4-hydroxy-2-isopropyl-5-methylphenoxy)ethylamine hydrochloride N-Methyl-2-(4-hydroxy-2-isopropyl-5-methylphenoxy) ethylamine hydrochloride (10.4 g), 2-ethoxy-5-hydroxy-3,4,6-trimethylbenzyl chloride (9.15 g) and triethylamine (8.10 g) were dissolved in N,N-dimethylformamide (80 ml), and the mixture was stirred at room temperature for 4 hours. After the reaction, the solvent was distilled off and water was added. The mixture was extracted with ethyl acetate, and the extract was washed with saturated brine and dried over anhydrous sodium sulfate. The solvent was distilled off under reduced pressure. The resulting liquid (1.0 g) was dissolved in methanol and conc. hydrochloric acid (0.2 ml) was added. The mixture was concentrated to dryness under reduced pressure. Recrystallization from ethanol-diethyl ether gave 910 mg of the title compound.

Melting point: gradually decomposed from 140° C.

IR(KBr) $cm^{-1}$: 3190, 2980, 1600, 1505, 1460, 1415, 1395, 1285, 1265, 1210, 1140, 1085, 1065, 1025, 955, 910, 885, 810

NMR(DMSO-$d_6$) δ: 9.62(1H,brs), 8.85(1H,s), 8.23(1H, s), 6.72(1H,s), 6.69(1H,s), 4.54–4.23(4H,m), 3.73–3.55(4H, m), 3.17(1H,m), 2.74(3H,d), 2.27(3H,s), 2.13(6H,s), 2.09 (3H,s), 1.34(3H,t), 1.09(6H,d)

Elemental analysis ($C_{25}H_{37}NO_4 \cdot HCl$) Calculated: C,66.43; H,8.47; N,3.10; Cl,7.84 Found: C,66.17; H,8.43; N,3.19; Cl,7.93

Example 5

Synthesis of N-(3-acetoxy-6-ethoxy-2,4,5-trimethylbenzyl)-N-methyl-2-(4-acetoxy-2-isopropyl-5-methylphenoxy)ethylamine monofumarate N-(2-Ethoxy-5-hydroxy-3,4,6-trimethylbenzyl)-N-methyl-2-(4-hydroxy-2-isopropyl-5-methylphenoxy) ethylamine (3.16 g) was dissolved in methylene chloride, and acetic anhydride (21.4 g) and pyridine (1.66 g) were added dropwise. The mixture was refluxed under heating for 14 hours. After the reaction, the solvent was distilled off and water was added. The mixture was extracted with ethyl acetate, and the extract was washed with saturated brine and dried over anhydrous sodium sulfate. The solvent was distilled off under reduced pressure. The resulting liquid was treated by silica gel chromatography (eluent; ethyl acetate/benzene=1/9) to give 2.0 g of a colorless liquid. The liquid was dissolved in ethanol and fumaric acid (0.23 g) was added. The mixture was concentrated to dryness under reduced pressure to give 2.02 g of the title compound.

Melting point: gradually decomposed from 60° C.

IR(KBr) $cm^{-1}$: 3450, 2980, 1755, 1675, 1615, 1505, 1460, 1370, 1215, 1185, 1145, 1065, 1025, 985, 910, 805, 650

NMR(DMSO-$d_6$) δ: 6.80(1H,s), 6.79(1H,s), 6.62(2H,s), 4.01 (2H,t), 3.72(2H,q), 3.58(2H,s), 3.13(1H,m), 2.77(2H,t), 2.32(3H,s), 2.25(3H,s), 2.23(3H,s), 2.14(3H,s), 2.10(3H,s), 2.03(3H,s), 1.98(3H,s), 1.33(3H,t), 1.08(6H,d)

Elemental analysis ($C_{29}H_{41}NO_6 \cdot C_4H_4O_4 \cdot H_2O$) Calculated: C,62.54; H,7.47; N,2.21 Found: C,62.85; H,7.32; N,2.22

Example 6

Synthesis of N-(2-diethylaminoethyl)-N-(3-hydroxy-6-methoxy-2,4,5-trimethylbenzyl)-2-(2-isopropyl-5-methylphenoxy)ethylamine dihydrochloride N-{2-(2-Isopropyl-5-methylphenoxy)ethyl}N', N'-diethylethylenediamine (5.85 g) and 3-hydroxy-6-methoxy-2,4,5-trimethylbenzyl chloride (4.29 g) were dissolved in N,N-dimethylformamide (70 ml), and triethylamine (2.02 g) was added dropwise while stirring the mixture at room temperature. The mixture was stirred for 14 hours. After the reaction, the solvent was distilled off, and water was added. The mixture was extracted with ethyl acetate. The obtained organic layer was washed with saturated brine and dried over anhydrous sodium sulfate, and the solvent was distilled off under reduced pressure. The obtained liquid was purified by silica gel chromatography (eluent; ethyl acetate) to give 6.08 g of a colorless liquid. The liquid was dissolved in methanol and conc. hydrochloric acid (1.07 ml) was added. The mixture was concentrated to dryness under reduced pressure and recrystallized from ethanol-ethyl acetate-diethyl ether to give 5.74 g of the title compound (colorless crystals).

Melting point: gradually decomposed from 163° C.

IR(KBr) $cm^{-1}$: 3480, 2980, 2650, 1610, 1575, 1510, 1455, 1420, 1300, 1265, 1225, 1175, 1125, 1085, 1060, 1030, 980, 950, 820, 670, 600

NMR(DMSO-$d_6$) δ: 11.39(1H,brs), 10.27(1H, brs), 7.08 (1H,d), 6.78(1H,s), 6.75(1H,d), 4.51 (4H,m), 3.71 (4H,m), 3.61 (3H,s), 3.13(5H,m), 2.32(3H,s), 2.27(3H,s), 2.14(6H, s), 1.24(6H,m), 1.10(6H,d)

Elemental analysis ($C_{29}H_{45}N_2O_3 \cdot 2HCl$) Calculated: C,64.07; H,8.90; N,5.15; Cl,13.04 Found: C,63.82; H,8.89; N,5.28; Cl,13.11

Example 7

Synthesis of N-ethyl-N-(3-hydroxy-6-methoxy-2,4, 5-trimethylbenzyl)-2-(4-chloro-2-isopropyl-5-methylphenoxy)ethylamine hydrochloride N-Ethyl-2-(4-chloro-2-isopropyl-5-methylphenoxy) ethylamine (6.42 g) and 3-hydroxy-6-methoxy-2,4,5-trimethylbenzyl chloride (5.39 g) were dissolved in N,N-dimethylformamide (100 ml), and triethylamine (2.53 g) was added dropwise while stirring the mixture at room temperature. The mixture was stirred for 14 hours. After the reaction, the solvent was distilled off, and water was added. The mixture was neutralized with sodium hydrogencarbonate and extracted with ethyl acetate. The obtained organic layer was washed with saturated brine and dried over anhydrous sodium sulfate, and the solvent was distilled off under reduced pressure. The obtained liquid was purified by silica gel chromatography (eluent; ethyl acetate/benzene=1/4) to give 4.57 g of a colorless liquid. The liquid was dissolved in methanol and conc. hydrochloric acid (1 ml) was added. The mixture was concentrated to dryness under reduced pressure and recrystallized from ethanol-ethyl acetate to give 3.31 g of the title compound (colorless crystals).

Melting point: 203°–205° C.

IR(KBr) $cm^{-1}$: 3350, 3160, 2980, 1605, 1460, 1395, 1350, 1290, 1255, 1225, 1210, 1175, 1130, 1085, 1065, 1040, 960, 880, 845, 810, 770, 645

NMR(DMSO-$d_6$) δ: 9.15(1H,brs), 8.25(1H,s), 7.18(1H,s), 6.97(1H,s), 4.41 (4H,m), 3.61 (3H,s), 3.52(2H,m), 3.28 (4H,m), 3.13(1H,m), 2.29(3H,s), 2.26(3H,s), 2.14(6H,s), 1.37(3H,t), 1.11 (6H,dd)

Elemental analysis ($C_{25}H_{36}NO_3Cl \cdot HCl$) Calculated: C,63.82; H,7.93; N,2.98; Cl,15.07 Found: C,64.26; H,7.93; N,3.02; Cl,14.06

Example 8

Synthesis of N-{2-(2-isopropyl-5-methylphenoxy) ethyl{-N-(2,5-dimethoxy-3,4,6-trimethylbenzyl) acetamide 60% Sodium hydride (2 g) was washed with n-hexane under a nitrogen atmosphere, and suspend in tetrahydrofuran (50 ml) at room temperature, during which a solution of N-{2-(2-isopropyl-5-methylphenoxy)ethyl}acetamide (11.7 g) dissolved in tetrahydrofuran (50 ml) was added dropwise. Then, a solution of 2,5-dimethoxy-3,4,6-trimethylbenzyl chloride (11.5 g) dissolved in tetrahydrofuran (10 ml) was added dropwise, and the mixture was refluxed under heating for 12 hours. After the reaction, the solvent was distilled off and water was added. The mixture was extracted with ethyl acetate, and the obtained organic layer was washed with saturated brine and dried over anhydrous sodium sulfate. The solvent was distilled off under anhydrous sodium sulfate. The solvent was distilled off under reduced pressure. The resulting liquid was purified by silica gel column chromatography (eluent; ethyl acetate/benzene=1/9) to give 15.2 g of a pale-yellow solid. The obtained pale-yellow solid was recrystallized from n-hexane—isopropyl alcohol to give 10.1 g of the title compound (colorless crystals).

Melting point: 103°–106° C.

IR(KBr) $cm^{-1}$: 2970, 2930, 2880, 1655, 1610, 1580, 1510, 1450, 1390, 1350, 1290, 1265, 1170, 1120, 1090, 1075, 1005, 965, 930, 855, 810, 745, 665, 615, 595, 495

NMR(CDCl$_3$) δ: 7.08(1H,d), 6.75(1H,d), 6.55(1H,s), 4.82 (2H,s), 3.90(2H,t), 3.62(3H,s), 3.58(3H,s), 3.45(2H,t), 3.20 (1H,m), 2.31(3H,s), 2.29(3H,s), 2.27(3H,s), 2.20(6H,s), 1.17(6H,d)

Elemental analysis ($C_{26}H_{37}NO_4$) Calculated: C,73.04; H,8.72; N,3.28 Found: C,72.97; H,8.74; N,3.24

Example 9

Synthesis of N-(3-hydroxy-6-methoxy-2,4,5-trimethylbenzyl)-N-methyl-2-(4-acetyl-2-isopropyl-5-methylphenoxy)ethylamine N-Methyl-2-(4-acetyl-2-isopropyl-5-methylphenoxy) ethylamine (6.75 g) and 3-hydroxy-6-methoxy-2,4,5-trimethylbenzyl chloride (5.48 g) were dissolved in N,N-dimethylformamide (80 ml), and triethylamine (2.58 g) was added dropwise while stirring the mixture at room temperature. The mixture was stirred at room temperature for 16.5 hours. After the reaction, the solvent was distilled off, and water was added. The mixture was extracted with ethyl acetate. The obtained organic layer was washed with saturated brine and dried over anhydrous sodium sulfate, and the solvent was distilled off under reduced pressure. The obtained liquid was purified by silica gel chromatography (eluent; ethyl acetate/benzene=1/1) to give 10.38 g of a pale-yellow solid. The obtained solid was recrystallized from isopropyl alcohol to give 7.22 g of the title compound (colorless crystals).

Melting point: 109°–114° C.

IR(KBr) $cm^{-1}$: 3210, 2960, 2940, 2870, 1680, 1610, 1560, 1515, 1465, 1375, 1355, 1315, 1265, 1170, 1135, 1120, 1100, 1085, 1055, 1010, 975, 950, 900, 850, 800, 755, 675, 595

NMR(CDCl$_3$) δ: 7.59(1H,s), 6.60(1H,s), 4.55(1H,brs), 4.09(2H,t), 3.64(3H,s), 3.60(2H,s), 3.24(1H,m), 2.85(2H,t), 2.55(3H,s), 2.52(3H,s), 2.31(3H,s), 2.26(3H,s), 2.20(3H,s), 2.17(3H,s), 1.19(6H,d)

Elemental analysis ($C_{26}H_{37}NO_4$) Calculated: C,73.04; H,8.72; N,3.28 Found: C,72.78; H,8.89; N,3.15

Example 10

Synthesis of N-(2,5-dimethoxy-3,4,6-trimethylbenzyl)-N-methyl-2-(4-acetylamino-2-isopropyl-5-methylphenoxy)ethylamine N-Methyl-2-(4-acetylamino-2-isopropyl-5-methylphenoxy)ethylamine (4.94 g) and 2,5-dimethoxy-3,4,6-trimethylbenzyl chloride (4.29 g) were dissolved in N,N-dimethylformamide (70 ml), and triethylamine (1.89 g) was added dropwise while stirring the mixture at room temperature. The mixture was stirred at room temperature for 16.5 hours. After the reaction, the solvent was distilled off, and water was added. The mixture was extracted with ethyl acetate. The obtained organic layer was washed with saturated brine and dried over anhydrous sodium sulfate, and the solvent was distilled off under reduced pressure. The obtained crude product was purified by silica gel chromatography (eluent; ethyl acetate/benzene=1/1) to give 6.40 g of a pale-yellow solid. A portion (1.0 g) was taken therefrom and recrystallized from diisopropyl ether to give 0.62 g of the title compound (colorless crystals).

Melting point: 114.5°–116° C.

IR(KBr) $cm^{-1}$: 3500, 3280, 2940, 1650, 1535, 1510, 1460, 1405, 1370, 1290, 1260, 1210, 1155, 1090, 1050, 1020, 895, 850, 805

NMR(CDCl$_3$) δ: 7.25(1H,s), 6.85(1H,dd), 6.62(1H,s), 4.02(2H,t), 3.67(3H,s), 3.64(3H,s), 3.58(2H,s), 3.23(1H,m), 2.83(2H,t), 2.32(3H,s), 2.28(3H,s), 2.19(3H,s), 2.18(3H,s), 2.16(3H,s), 1.15(6H,d)

Elemental analysis (C$_{27}$H$_{40}$N$_2$O$_4$) Calculated: C.71.02; H.8.83; N.6.13 Found: C.70.76; H.8.93; N.6.07

Example 11

Synthesis of N-(2,5-dimethoxy-3,4,6-trimethylbenzyl)-N-methyl-2-(4-amino-2-isopropyl-5-methylphenoxy)ethylamine dihydrochloride N-(2,5-Dimethoxy-3,4,6-trimethylbenzyl)-N-methyl-2-(4-acetylamino-2-isopropyl-5-methylphenoxy)ethylamine (5.40 g) was dissolved in conc. hydrochloric acid (20 ml) and water (27 ml), and the mixture was refluxed under heating for 1 hour. After the reaction, the reaction mixture was made basic with sodium hydroxide and extracted with ethyl acetate. The obtained organic layer was washed with saturated brine and dried over anhydrous sodium sulfate, and the solvent was distilled off under reduced pressure to give 5.0 g of a red brown liquid. The liquid was dissolved in methanol and conc. hydrochloric acid (2 ml) was added. The mixture was concentrated to dryness under reduced pressure and recrystallized from ethanol-ethyl acetate to give 5.31 g of the title compound (white powder).

Melting point: 234°–235° C.

IR(KBr) cm$^{-1}$: 3450, 3140, 2900, 2550, 1625, 1570, 1515, 1460, 1395, 1280, 1260, 1245, 1220, 1195, 1140, 1115, 1090, 1065, 1035, 1010, 950, 905

NMR(DMSO-d$_6$) δ: 10.20(1H,brs), 9.92(1H, brs), 7.40 (1H,s), 6.97(1H,s), 4.45(4H,m), 3.63(3H,s), 3.59(3H,s), 3.42(2H,m), 3.25(1H,m), 2.77(3H,s), 2.36(3H,s), 2.35(3H, s), 2.18(3H,s), 2.16(3H,s), 1.13(6H,d)

Elemental analysis (C$_{25}$H$_{36}$N$_2$O$_3$.2HCl) Calculated: C.61.59; H.8.27; N.5.75; Cl.14.54 Found: C.61.60; H.8.45; N.5.71; Cl.14.41

Example 12

Synthesis of N-(3-hydroxy-6-methoxy-2,4,5-trimethylbenzyl)-N-methyl-2-(2-isopropyl-5-methylphenoxy)ethylamine Triethylamine (7.0 ml) was added dropwise to a solution of 3-hydroxy-6-methoxy-2,4,5-trimethylbenzyl chloride (10.73 g) and N-methyl-2-(2-isopropyl-5-methylphenoxy) ethylamine (10.37 g) in N,N-dimethylformamide (60 ml) while stirring the mixture at room temperature. Immediately after the dropwise addition, heat was developed and salt was precipitated. The mixture was stirred at room temperature for 2 hours and triethylamine (2.0 ml) was added. The mixture was stirred for 1 hour. The reaction mixture was poured on ice water and extracted with ethyl acetate to give a crude product. The product was purified by silica gel chromatography (eluent; ethyl acetate/benzene=1/1) to give 18.03 g of the title compound (pale brown solid).

Melting point: 75°–77° C.

IR(KBr) cm$^{-1}$: 3420, 2940, 2860, 1605, 1570, 1455, 1345, 1285, 1250, 1170, 1090, 1065, 1000, 970, 945, 855, 805, 755, 605

NMR(CDCl$_3$) δ: 7.08(1H,d), 6.72(1H,d), 6.63(1H,s), 4.60 (1H,brs), 4.05(2H,t), 3.64(3H,s), 3.60(2H,s), 3.29(1H,m), 2.85(2H,t), 2.29(6H,s), 2.26(3H,s), 2.20(3H,s), 2.16(3H,s), 1.16(6H,d)

Elemental analysis (C$_{24}$H$_{35}$NO$_3$) Calculated: C.74.77; H.9.15; N.3.63 Found: C.74.50; H.9.22; N.3.42

Example 13

Synthesis of N-(3-benzyloxy-6-methoxy-2,4,5-trimethylbenzyl)-N-methyl-2-(2-isopropyl-5-methylphenoxy)ethylamine 3/2 fumarate Metallic sodium (0.35 g) was dissolved in dry ethanol (70 ml), and N-(3-hydroxy-6-methoxy-2,4,5-trimethylbenzyl)-N-methyl-2-(2-isopropyl-5-methylphenoxy)ethylamine (4.00 g) was added. The mixture was stirred for 30 minutes and benzyl bromide (1.4 ml) was added dropwise. The mixture was refluxed under heating for 16 hours. After the completion of the reaction and cooling the reaction mixture, water was added and the mixture was concentrated to give an aqueous layer only. The mixture was extracted with ethyl acetate and the obtained crude product was purified by silica gel column chromatography (eluent; ethyl acetate/benzene= 1/1) to give 3.09 g of a yellow oil.

NMR(CDCl$_3$) δ: 7.40(5H,m), 7.05(1H,d), 6.72(1H,d), 6.65(1H,s), 4.71(2H,s), 4.05(2H,t), 3.59(3H,s), 3.61(2H,s), 3.30(1H,m), 2.86(2H,t), 2.36(3H,s), 2.30(6H,s), 2.23(3H,s), 2.20(3H,s), 1.17(6H,d)

The oil was dissolved in ethanol and fumaric acid (0.74 g) was added. The mixture was heated for dissolution. After the solvent was distilled off, the residue was recrystallized from ethyl acetate-n-hexane to give 2.42 g of the title compound (colorless crystals).

Melting point: 138°–141° C.

IR(KBr) cm$^{-1}$: 2950, 2500, 1730, 1680, 1600, 1450, 1380, 1365, 1250, 1160, 1075, 975

NMR(DMSO-d$_6$) δ: 7.45(5H,m), 7.05(1H,d), 6.70(1H,s), 6.69(1H,d), 6.62(3H,s), 4.66(2H,s), 4.04(2H,t), 3.65(2H,s), 3.61(3H,s), 3.19(1H,m), 2.87(2H,t), 2.30(3H,s), 2.28(3H,s), 2.23(3H,s), 2.18(3H,s), 2.14(3H,s), 1.08(6H,d)

Elemental analysis (C$_{31}$H$_{41}$NO$_3$.3/2C$_4$H$_4$O$_4$.1/2H$_2$O) Calculated: C.67.46; H.7.34; N.2.13 Found: C.67.14; H.7.44; N.1.93

Example 14

Synthesis of N-(3-isopropoxy-6-methoxy-2,4,5-trimethylbenzyl)-N-methyl-2-(2-isopropyl-5-methylphenoxy)ethylamine p-toluenesulfonate Metallic sodium (0.35 g) was dissolved in dry ethanol (50 ml), and N-(3-hydroxy-6-methoxy-2,4,5-trimethylbenzyl)-N-methyl-2-(2-isopropyl-5-methylphenoxy)ethylamine (4.00 g) was added. The mixture was stirred for 30 minutes and isopropyl iodide (1.2 ml) was added dropwise. The mixture was refluxed under heating for 16 hours. After cooling the reaction mixture, water was added and ethanol was distilled off. The residue was extracted with ethyl acetate and the obtained crude product was purified by silica gel column chromatography (eluent; ethyl acetate/benzene= 1/1) to give 1.65 g of a slightly yellow oil.

NMR(CDCl$_3$) δ: 7.08(1H,d), 6.72(1H,d), 6.62(1H,s), 4.03 (3H,m), 3.67(3H,s), 3.59(2H,s), 3.28(1H,m), 2.31(3H,s), 2.29(3H,s), 2.28(3H,s), 2.17(6H,s), 1.26(6H,d), 1.16(6H,d)

The oil was dissolved in ethanol and p-toluenesulfonic acid monohydrate (0.67 g) was added. The mixture was heated for dissolution. After the solvent was distilled off, the residue was recrystallized from ethyl acetate-n-hexane to give 1.58 g of the title compound (slightly yellow needle crystals).

Melting point: 120°–122° C.

IR(KBr) cm$^{-1}$: 2970, 1610, 1455, 1405, 1255, 1230, 1170, 1120, 1030, 1005, 810, 680, 555

NMR(DMSO-d$_6$) δ: 8.85(1H,brs), 7.48(2H,d), 7.08(3H, d), 6.79(1H,s), 6.76(1H,d), 4.54(1H,dd), 4.38(3H,brs), 4.00 (1H,m), 3.64(5H,brs), 3.23(1H,m), 2.80(3H,d), 2.27(9H,s), 2.16(6H,s), 1.20(6H,d), 1.11(6H,m)

Elemental analysis (C$_{27}$H$_{41}$NO$_3$·C$_7$H$_8$SO$_3$) Calculated: C,68.08; H,8.23; N,2.34; S,5.35 Found: C,67.85; H,8.36; N,2.15; S,5.33

Example 15

Synthesis of N-(3-ethoxy-6-methoxy-2,4,5-trimethylbenzyl)-N-methyl-2-(2-isopropyl-5-methylphenoxy)ethylamine ½ fumarate Metallic sodium (0.35 g) was dissolved in dry ethanol (70 ml), and N-(3-hydroxy-6-methoxy-2,4,5-trimethylbenzyl)-N-methyl-2-(2-isopropyl-5-methylphenoxy)ethylamine (4.00 g) was added. After stirring the mixture for 30 minutes, ethyl iodide (1.2 ml) was added dropwise and the mixture was refluxed under heating for 16 hours. After cooling the reaction mixture, water was added and ethanol was distilled off. The residue was extracted with ethyl acetate and the obtained crude product was purified by silica gel column chromatography (eluent; ethyl acetate/benzene=1/1) to give 3.46 g of a slightly yellow oil.

NMR(CDCl$_3$) δ: 7.08(1H,d), 6.72(1H,d), 6.63(1H,s), 4.04 (2H,t), 3.72(2H,q), 3.66(3H,s), 3.59(2H,s), 3.28(1H,m), 2.85(2H,t), 2.32(3H,s), 2.29(6H,s), 2.18(6H,s), 1.40(3H,t), 1.16(6H,d)

The oil was dissolved in ethanol and fumaric acid (0.41 g) was added. The mixture was heated for dissolution. After the solvent was distilled off, the residue was recrystallized from ethyl acetate-ethanol to give 1.95 g of the title compound (colorless crystals).

Melting point: 115°–120° C.

IR(KBr) cm$^{-1}$: 2960, 1715, 1610, 1455, 1410, 1290, 1255, 1165, 1080, 1060, 1030, 980, 810, 640

NMR(DMSO-d$_6$) δ: 7.03(1H,d), 6.69(1H,s), 6.68(1H,d), 6.63(2H,s), 4.04(2H,t), 3.64(2H,q), 3.63(2H,s), 3.58(3H,s), 3.19(1H,m), 2.85(2H,t), 2.27(3H,s), 2.25(3H,s), 2.23(3H,s), 2.12(6H,s), 1.31(3H,t), 1.09(6H,d)

Elemental analysis (C$_{26}$H$_{39}$NO$_3$·½C$_4$H$_4$O$_4$·¾H$_2$O) Calculated: C,68.06; H,8.87; N,2.83 Found: C,67.98; H,8.69; N,2.61

Example 16

Synthesis of N-{3-hydroxy-6-(2-hydroxyethoxy)-2,4,5-trimethylbenzyl}-N-methyl-2-(2-isopropyl-5-methylphenoxy)ethylamine Triethylamine (2.1 ml) was added dropwise to a solution of 3-hydroxy-6-(2-hydroxyethoxy)-2,4,5-trimethylbenzyl chloride (2.45 g) and N-methyl-2-(2-isopropyl-5-methylphenoxy)ethylamine (2.07 g) in N,N-dimethylformamide (30 ml), and the mixture was stirred at room temperature for 16 hours. The reaction mixture was poured on ice water and extracted with ethyl acetate. The obtained extract was purified by silica gel column chromatography (eluent; ethyl acetate/benzene=1/1) and recrystallized from methanol-water to give 2.51 g of the title compound (colorless needle crystals).

Melting point: 115°–118° C.

IR(KBr) cm$^{-1}$: 3050, 2955, 2930, 2865, 2670, 1610, 1505, 1455, 1410, 1280, 1255, 1240, 1085, 1055, 875, 810

NMR(DMSO-d$_6$) δ: 7.70(1H,brs), 7.03(1H,d), 6.69(1H, s), 6.67(1H,d), 4.90(1H,brs), 4.02(2H,t), 3.66(4H,brs), 3.53 (2H,s), 3.19(1H,m), 2.74(2H,t), 2.23(3H,s), 2.19(6H,s), 2.11 (3H,s), 2.08(3H,s), 1.09(6H,d)

Elemental analysis (C$_{25}$H$_{37}$NO$_4$) Calculated: C,72.26; H,8.97; N,3.37 Found: C,71.99; H,9.11; N,3.29

Example 17

Synthesis of N-{3-acetoxy-6-(2-propenyloxy)-2,4,5-trimethylbenzyl}-N-methyl-2-(2-isopropyl-5-methylphenoxy)ethylamine ½ fumarate Triethylamine (2.1 ml) was added dropwise to a solution of 3-acetoxy-6-(2-propenyloxy)-2,4,5-trimethylbenzyl chloride (2.83 g) and N-methyl-2-(2-isopropyl-5-methylphenoxy)ethylamine (2.07 g) in N,N-dimethylformamide (30 ml), and the mixture was stirred at room temperature for 16 hours. The reaction mixture was poured on ice water and extracted with ethyl acetate. The obtained extract was purified by silica gel column chromatography (eluent; ethyl acetate/benzene=1/1) to give 3.13 g of a pale-brown oil.

NMR(CDCl$_3$) δ: 7.08(1H,d), 6.73(1H,d), 6.63(1H,s), 6.11 (1H,m), 5.47(1H,m), 5.27(1H,m), 4.38(2H,d), 4.03(2H,t), 3.59(2H,s), 3.27(1H,m), 2.85(2H,t), 2.33(3H,s), 2.29(6H,s), 2.18(6H,s), 2.04(3H,s), 1.16(6H,d)

The oil (2.93 g) was dissolved in ethyl acetate and heated together with fumaric acid (0.70 g) for dissolution. The solvent was distilled off under reduced pressure. The residue was recrystallized from a mixed solvent of ethyl acetate-n-hexane to give 2.12 g of the title compound (colorless crystals).

Melting point: 155°–156° C.

IR(KBr) cm$^{-1}$: 2960, 1755, 1700, 1625, 1450, 1410, 1370, 1290, 1250, 1200, 1075, 1055, 970, 640

NMR(DMSO-d$_6$) δ: 7.04(1H,d), 6.70(1H,s), 6.68(1H,d), 6.65(3H,s), 6.11(1H,m), 5.48(1H,m), 5.25(1H,m), 4.28(2H, d), 4.07(2H,t), 3.71(2H,s), 3.20(1H,m), 2.92(2H,t), 2.33(3H, s), 2.31(3H,s), 2.24(3H,s), 2.15(3H,s), 2.13(3H,s), 2.00(3H, s), 1.09(6H,d)

Elemental analysis (C$_{28}$H$_{38}$NO$_4$·½C$_4$H$_4$O$_4$) Calculated: C,65.06; H,7.23; N,2.23 Found: C,65.13; H,7.25; N,2.22

Example 18

Synthesis of N-(3-acetoxy-6-isopropoxy-2,4,5-trimethylbenzyl)-N-ethyl-2-(4-chloro-2-isopropyl-5-methylphenoxy)ethylamine monofumarate Triethylamine (1.4 ml) was added dropwise to a solution of 3-acetoxy-6-isopropoxy-2,4,5-trimethylbenzyl chloride (2.36 g) and N-ethyl-2-(4-chloro-2-isopropyl-5-methylphenoxy)ethylamine (2.56 g) in N,N-dimethylformamide (30 ml), and the mixture was stirred at room temperature for 16 hours. The reaction mixture was poured on ice water and extracted with ethyl acetate. The obtained extract was purified by silica gel column chromatography (eluent; ethyl acetate/benzene=1/1) to give 3.61 g of a pale-brown oil.

NMR(CDCl$_3$) δ: 7.09(1H,s), 6.58(1H,m), 4.00(1H,m), 3.87(2H,t), 3.68(2H,s), 3.22(1H,m), 2.79(2H,t), 2.60(2H,q), 2.32(3H,s), 2.28(3H,s), 2.16(6H,s), 2.03(3H,s), 1.24(6H,d), 1.14(6H,d), 1.06(3H,t)

The oil (3.12 g) was dissolved in ethyl acetate and heated together with fumaric acid (0.70 g) for dissolution. The solvent was distilled off under reduced pressure. The residue was recrystallized from a mixed solvent of ethyl acetate-n-hexane to give 0.91 g of the title compound (colorless crystals).

Melting point: 156°–157° C.

IR(KBr) cm$^{-1}$: 2975, 2645, 1760, 1710, 1450, 1300, 1250, 1210, 1175, 1080, 645

NMR(DMSO-d$_6$) δ: 7.09(1H,s), 6.82(1H,s), 6.63(3H,s), 3.97(3H,s), 3.70(2H,s), 3.14(1H,m), 2.75(2H,t), 2.50(2H, m), 2.31(3H,s), 2.24(3H,s), 2.12(3H,s), 2.10(3H,s), 1.97(3H,s), 1.19(6H,d), 1.09(6H,d), 1.00(3H,t)

Elemental analysis (C$_{29}$H$_{42}$NO$_4$Cl.C$_4$H$_4$O$_4$.½H$_2$O) Calculated: C,63.00; H,7.53; N,2.23 Found: C,62.60; H,7.35; N,2.11

Example 19

Synthesis of N-(3-ethoxy-6-hydroxy-2,4,5-trimethylbenzyl)-2-(2-isopropyl-5-methylphenoxy) ethylamine A solution of 3-ethoxy-6-hydroxy-2,4,5-trimethylbenzaldehyde (2.08 g) and 2-(2-isopropyl-5-methylphenoxy)ethylamine (1.93 g) in benzene (50 ml) was refluxed under heating for 6 hours in a Dean-Stark extractor. The solvent was distilled off under reduced pressure and the residue was suspended in ethanol (100 ml). Sodium borohydride (0.40 g) was added with ice-cooling and the mixture was stirred at room temperature for 16 hours. The solvent was distilled off under reduced pressure and water was added. The mixture was extracted with ethyl acetate and the obtained extract was purified by silica gel column chromatography (eluent; ethyl acetate/benzene=1/1) to give 3.06 g of a colorless solid. The solid was recrystallized from a mixed solvent of ethanol-methanol to give 1.99 g of the title compound (colorless needle crystals).

Melting point: 99°–101° C.

IR(KBr) cm$^{-1}$: 3320, 2950, 2860, 1600, 1500, 1455, 1410, 1380, 1285, 1250, 1160, 1080, 1035, 895, 800

NMR(CDCl$_3$) δ: 7.10(1H,d), 6.75(1H,d), 6.65(1H,s), 4.08(4H,m), 3.70(2H,q), 3.28(1H,m), 3.07(2H,t), 2.32(3H,s), 2.19(6H,s), 2.13(3H,s), 1.39(3H,t), 1.19(6H,d)

Elemental analysis (C$_{24}$H$_{35}$NO$_3$) Calculated: C,74.77; H,9.15; N,3.63 Found: C,74.62; H,9.23; N,3.48

Example 20

Synthesis of N-(2-benzyloxy-5-ethoxy-3,4,6-trimethylbenzyl)-2-(2-isopropyl-5-methylphenoxy) ethylamine A solution of 2-benzyloxy-5-ethoxy-3,4,6-trimethylbenzaldehyde (2.98 g) and 2-(2-isopropyl-5-methylphenoxy)ethylamine (1.93 g) in benzene (50 ml) was refluxed under heating for 5 hours in a Dean-Stark extractor. The solvent was distilled off under reduced pressure and the residue was suspended in ethanol (100 ml). Sodium borohydride (0.40 g) was added with ice-cooling and the mixture was stirred at room temperature for 16 hours. The solvent was distilled off under reduced pressure and water was added. The mixture was extracted with ethyl acetate and the obtained extract was purified by silica gel column chromatography (eluent; ethyl acetate/benzene=1/1) to give 4.16 g of a colorless solid. The solid was recrystallized from methanol to give 1.62 g of the title compound (colorless needle crystals).

Melting point: gradually decomposed from 60° C.

IR(KBr) cm$^{-1}$: 2955, 2910, 2850, 1600, 1495, 1445, 1375, 1245, 1160, 1075, 1050, 1030, 805, 735, 685

NMR(CDCl$_3$) δ: 7.40(5H,m), 7.05(1H,d), 6.71(1H,d), 6.60(1H,s), 4.83(2H,s), 4.03(2H,t), 3.88(2H,s), 3.76(2H,q), 3.22(1H,m), 3.02(2H,t), 2.31(3H,s), 2.28(3H,s), 2.22(3H,s), 2.20(3H,s), 1.42(3H,t), 1.12(6H,d)

Elemental analysis (C$_{31}$H$_{41}$NO$_3$) Calculated: C,78.28; H,8.69; N,2.94 Found: C,78.21; H,8.85; N,2.86

Example 21

Synthesis of N-(3-hydroxy-6-methoxy-2,4,5-trimethylbenzyl)-2-(4-hydroxy-2-isopropyl-5-methylphenoxy)ethylamine hydrochloride A solution of 3-hydroxy-6-methoxy-2,4,5-trimethylbenzaldehyde (1.94 g) and 2-(4-acetoxy-2-isopropyl-5-methylphenoxy)ethylamine (2.51 g) in benzene (50 ml) was refluxed under heating for 6 hours in a Dean-Stark extractor. The solvent was distilled off under reduced pressure and the residue was suspended in ethanol (100 ml). Sodium borohydride (0.40 g) was added with ice-cooling and the mixture was stirred at room temperature for 16 hours. The solvent was distilled off under reduced pressure and water was added. The mixture was extracted with ethyl acetate, and the obtained extract was washed with water, dried and concentrated to give 2.3 g of a pale-brown oil. The oil was dissolved in methanol (50 ml) and conc. hydrochloric acid (2 ml) was added. The mixture was refluxed under heating for 5 hours. After cooling, the solvent was distilled off under reduced pressure. The residue was recrystallized from ethanol-diethyl ether to give 1.45 g of the title compound (colorless crystals).

Melting point: gradually decomposed from 195° C.

IR(KBr) cm$^{-1}$: 3400, 2960, 1620, 1510, 1465, 1415, 1290, 1265, 1210, 1090, 1010, 930, 880, 815

NMR(DMSO-d$_6$) δ: 8.82(2H,brs), 8.80(1H,s), 8.17(1H,s), 6.70(1H,s), 6.65(1H,s), 4.20(4H,m), 3.61 (3H,s), 3.34 (2H,m), 3.30(1H,m), 2.23(3H,s), 2.13(6H,s), 2.08 (3H,s), 1.10(6H,d)

Elemental analysis (C$_{23}$H$_{33}$NO$_4$.HCl.H$_2$O) Calculated: C,62.50; H,8.21; N,3.17; Cl,8.02 Found : C,62.46; H,7.99; N,3.18; Cl,7.81

Example 22

Synthesis of N-(3-hydroxy-6-methoxy-2,4,5-trimethylbenzyl)-N-isopropyl-2-(4-hydroxy-2-isopropyl-5-methylphenoxy)ethylamine hydrochloride Triethylamine (2.8 ml) was added dropwise to a solution of N-isopropyl-2-(4-acetoxy-2-isopropyl-5-methylphenoxy)ethylamine (2.93 g) and 3-hydroxy-6-methoxy-2,4,5-trimethylbenzyl chloride (2.15 g) in N,N-dimethylformamide (20 ml), and the mixture was stirred at room temperature for 16 hours. After the completion of the reaction, the reaction mixture was poured on ice water and extracted with ethyl acetate. The obtained extract was washed with water, dried and concentrated to give 4.43 g of a pale-brown oil. The oil was dissolved in methanol (50 ml) and conc. hydrochloric acid (2 ml) was added. The mixture was refluxed under heating for 5 hours. After cooling, the solvent was distilled off under reduced pressure. The residue was recrystallized from ethanol - diethyl ether to give 1.13 g of the title compound (colorless crystals).

Melting point: 222.4°–222.9° C.

IR(KBr) cm$^{-1}$: 3210, 3130, 2960, 1600, 1510, 1455, 1415, 1380, 1360, 1270, 1210, 1185, 1090, 1075, 1030, 970, 910, 870, 830, 740, 660, 600

NMR(DMSO-d$_6$) δ: 8.87(1H,brs), 8.68(1H,brs), 8.32(1H, brs), 6.69(1H,s), 6.58(1H,s), 4.51–4.13(4H,m), 3.76(1H,m), 3.60(3H,s), 3.50–3.22(2H,m), 3.09(1H,m), 2.28(3H,s), 2.14 (3H,s), 2.12(3H,s), 2.06(3H,s), 1.45(6H,dd), 1.09(6H,d)

Elemental analysis ($C_{26}H_{39}NO_4 \cdot HCl \cdot \frac{1}{4}H_2O$) Calculated: C,66.36; H,8.68; N,2.98; Cl,7.53 Found: C,66.48; H,8.64; N,3.00; Cl,7.57

Example 23

Synthesis of N-(3-hydroxy-6-methoxy-2,4,5-trimethylbenzyl)-N-(2-methoxyethyl)-2-(4-hydroxy-2-isopropyl-5-methlphenoxy)ethylamine hydrochloride Triethylamine (2) was added dropwise to a solution of N-(2-methoxyethyl)-2-(4-acetoxy-2-isoprpyl-5-methylphenoxy) ethylamine (4.38 g) and 3-hydroxy-6-methoxy-2,4,5-triemethylbenzyl chloride (3 g) in N,N-dimethylformamide (50 ml), and the mixture was stirred at room temperature for 16 hours. After the completion of the reaction, the reaction mixture was poured on ice water and extracted with ethyl acetate. The obtained extract was washed with water, dried and concentrated to give 4.2 g of a pale-brown oil. The oil was dissolved in methanol (50 ml) and conc. hydrochloric acid (2 ml) was added. The mixture was refluxed under heating for 5 hours. After cooling, the solvent was distilled off under reduced pressure. The residue was recrystallized from ethanol—diethyl ether to give 3.76 g of the title compound (colorless crystals).

Melting point: 198.6°–199.6° C.

IR(KBr) $cm^{-1}$: 3400, 3170, 2970, 1610, 1515, 1455, 1415, 1375, 1265, 1205, 1175, 1085, 1030, 970, 950, 870, 840, 820

NMR(DMSO-$d_6$) δ: 8.88(1H,s), 8.45(1H,brs), 8.33(1H, brs), 6.71(1H,s), 6.63(1H,s), 4.60(2H,m), 4.25(2H,s), 3.78 (2H,m), 3.58(3H,s), 3.46(4H,m), 3.26(3H,s), 3.16(1H,m), 2.27(3H,s), 2.13(3H,s), 2.10(3H,s), 2.06(3H,s), 1.09(6H,dd)

Elemental analysis ($C_{26}H_{39}NO_5 \cdot HCl$) Calculated: C,64.78; H,8.36; N,2.91; Cl,7.35 Found: C,64.49; H,8.28; N,2.92; Cl,7.33

Example 24

Synthesis of N-(3-hydroxy-6-propoxy-2,4,5-trimethylbenzyl)-N-methyl-2-(4-hydroxy-2-isopropyl-5-methylphenoxy)ethylamine ½ fumarate Triethylamine (2.8 ml) was added dropwise to a solution of N-methyl-2-(4-hydroxy-2-isopropyl-5-methylphenoxy) ethylamine hydrochloride (2.60 g) and 3-hydroxy-6-propoxy-2,4,5-trimethybenzyl chloride (2.43 g) in N,N-dimethylformamide (40 ml), and the mixture was stirred at room temperature for 16 hours. After the completion of the reaction, the reaction mixture was poured on ice water and extracted with ethyl acetate. The obtained extract was washed with water, dried and concentrated to give 3.79 g of a pale-brown oil. The oil was dissolved in a small amount of ethanol and fumaric acid (0.4 g) was added. The mixture was heated for dissolution. The solvent was distilled off under reduced pressure, and the residue was recrystallized from ethanol - diethyl ether to give 2.2 g of the title compound (colorless crystals).

Melting point: 176.4°–178.5° C.

IR(KBr) $cm^{-1}$: 3430, 2980, 2700, 1620, 1580, 1515, 1465, 1415, 1375, 1260, 1200, 1135, 1085, 1070, 1020, 955, 900, 880, 830, 755, 665, 575

NMR(DMSO-$d_6$) δ: 6.60(2H,s), 6.59(1H,s), 3.95(2H,s), 3.58(2H,s), 3.54(2H,t), 3.13(1H,m), 2.78(2H,t), 2.23(3H,s), 2.19(3H,s), 2.09(6H,s), 2.06(3H,s), 1.73(2H,m), 1.08(6H,d), 1.02(3H,t)

Elemental analysis ($C_{26}H_{39}NO_4 \cdot \frac{1}{2}C_4H_4O_4 \cdot \frac{1}{2}H_2O$) Calculated: C,67.72; H,8.52; N,2.82 Found: C,67.60; H,8.55: N,2.85

Example 25

Synthesis of N-tert-butyl-N-(3-hydroxy-6-methoxy-2,4,5-trimethylbenzyl)-2-(4-hydroxy-2-isopropyl-5-methylphenoxy)ethylamine hydrochloride Triethylamine (11.5 ml) was added dropwise to a solution of N-tert-butyl-2-(4-acetoxy-2-isopropyl-5-methylphenoxy) ethylamine (3.13 g) and 3-hydroxy-6-methoxy-2,4,5-trimethylbenzyl chloride (10.6 g) in N,N-dimethylformamide (50 ml), and the mixture was stirred at room temperature for 16 hours. After the completion of the reaction, the reaction mixture was poured on ice water and extracted with ethyl acetate. The obtained extract was washed with water, dried and concentrated to give 3.38 g of a pale-brown oil. The oil was dissolved in methanol and conc. hydrochloric acid (2 ml) was added. The mixture was refluxed under heating for 5 hours. After cooling, the solvent was distilled off under reduced pressure, and the residue was recrystallized from ethanol - diethyl ether to give 2.95 g of the title compound (colorless crystals).

Melting point: gradually decomposed from 188° C.

IR(KBr) $cm^{-1}$: 3150, 2990, 1600, 1520, 1455, 1415, 1380, 1360, 1330, 1270, 1205, 1180, 1080, 1030, 1010, 980, 885, 855, 835, 810, 740

NMR(DMSO-$d_6$) δ: 8.79(1H,s), 8.28(2H,s), 6.62(1H,s), 6.25(1H,s), 4.54(1H,d), 4.20(1H,dd), 3.72(1H,m), 3.62(3H, s), 3.55(1H,m), 3.35(1H,m), 2.90(2H,m), 2.32(3H,s), 2.11 (3H,s), 2.02(3H,s), 1.95(3H,s), 1.58(9H,s), 1.03(6H,dd)

Elemental anaylsis ($C_{27}H_{41}NO_4 \cdot HCl$) Calculated: C,67.55; H,8.82; N,2.92; Cl,7.38 Found: C,67.25; H,8.81; N,2.94; Cl,7.31

Example 26

Synthesis of N-(2-butoxy-5-hydroxy-3,4,6-trimethylbenzyl)-N-methyl-2-(4-hydroxy-2-isopropyl-5-methylphenoxy)ethylamine ½ fumarate Triethylamine (2.8 ml) was added dropwise to a solution of N-methyl-2-(4-hydroxy-2-isopropyl-5-methylphenoxy) ethylamine hydrochloride (2.60 g) and 2-butoxy-5-hydroxy-3,4,6-trimethylbenzyl chloride (2.57 g) in N,N-dimethylformamde (20 ml), and the mixture was stirred at room temperature for 16 hours. After the completion of the reaction, the reaction mixture was poured on ice water and extracted with ethyl acetate. The obtained extract was washed with water, dried and concentrated to give 3.25 g of a pale-brown oil. The oil was dissolved in a small amount of ethanol and fumaric acid (0.5 g) was added. The mixture was heated for dissolution. The solvent was distilled off under reduced pressure, and the residue was recrystallized from ethanol - diethyl ether to give 2.2 g of the title compound (colorless crystals).

Melting: 171.0°–173.7° C.

IR(KBr) $cm^{-1}$: 3450, 2970, 2680, 1615, 1580, 1580, 1515, 1465, 1420, 1395, 1365, 1260, 1200, 1130, 1085, 1015, 900, 875, 670

NMR(DMSO-$d_6$) δ: 6.59(2H,s), 6.58(1H,s), 3.92(2H,t), 3.57(2H,t), 3.53(2H,s), 3.12(1H,m), 2.73(2H,t), 2.20(3H,s), 2.18(3H,s), 2.08(6H,s), 2.05(3H,s), 1.68(2H,m), 1.49(2H, m), 1.07(6H,d), 0.93(3H,t)

Elemental analysis ($C_{27}H_{41}NO_4 \cdot \frac{1}{2}C_4H_4O_4 \cdot \frac{1}{4}H_2O$) Calculated: C,68.81; H,8.66; N,2.77 Found: C,69.04; H,8.92; N,2.78

Example 27

Synthesis of N-(3-acetoxy-6-hydroxy-2,4,5-trimethylbenzyl)-N-methyl-2-(4-hydroxy-2-isopropyl-5-methylphenoxy)ethylamine monofumarate Triethylamine (7 ml) was added dropwise to solution of N-methyl-2-(4-hydroxy-2-isopropyl-5-methylphenoxy)ethylamine hydrochloride (2.60 g) and 3-acetoxy-6-hydroxy-2,4,5-trimethylbenzyl chloride (8 g) in N,N-dimethylformamide (40 ml), and the mixture was stirred at room temperature for 16 hours. After the completion of the reaction, the reaction mixture was poured on ice water and extracted with ethyl acetate. The obtained extract was washed with water, dried and concentrated to give 3.7 g of a pale-brown oil. The oil was dissolved in a small amount of ethanol and fumaric acid (1.2 g) was added. The mixture was heated for dissolution. The solvent was distilled off under reduced pressure, and the residue was recrystallized from ethanol - diethyl ether to give 1.3 g of the title compound (colorless crystals).

Melting point: 151.3°–153.8° C.

IR(KBr) cm$^{-1}$: 3450, 1755, 1715, 1570, 1465, 1395, 1290, 1255, 1215, 1175, 1135, 1080, 1005, 985, 650

NMR(DMSO-d$_6$) δ: 6.71(2H,s), 6.62(2H,s), 3.96(2H,t), 3.71(2H,s), 3.58(2H,s), 3.18(1H,m), 2.73(2H,t), 2.25(3H,s), 2.20(3H,s), 2.12(3H,s), 2.11(3H,s), 2.08(3H,s), 1.11(6H,d)

Elemental analysis (C$_{25}$H$_{35}$NO$_5$. C$_4$H$_4$O$_4$) Calculated: C,63.84;H,7.20; N,2.56 Found: C,63.65; H,7.32; N,2.75

Example 28

Synthesis of N-(2,5-dimethoxy-3,4,6-trimethylbenzy)-N-methyl-2-(4-hydroxy-2-isopropyl-5-methylphenoxy)ethylamine ½ fumarate Triethylamine (5.6 ml) was added dropwise to a solution of N-methyl-2-(4-hydroxy-2-isopropyl-5-methylphenoxy)ethylamine hydrochloride (5.20 g) and 2,5-dimethoxy-3,4,6-trimethylbenzyl chloride (4.6 g) in N,N-dimethylformamide (50 ml), and the mixture was stirred at room temperature for 16 hours. After the completion of the reaction, the reaction mixture was poured on ice water and extracted with ethyl acetate. The obtained extract was washed with water, dried and concentrated to give 8.23 g of a pale-brown oil. The oil (1.8 g) was dissolved in ethanol and fumaric acid (1 g) was added. The mixture was heated for dissolution. The solvent was distilled off under reduced pressure, and the resdiue was recystallized from ethanol - diethyl ether to give 1.74 g of the title compound (colorless crystals).

Melting point: gradually decomposed from 85° C.

IR(KBr) cm$^{-1}$: 3430, 2970, 1700, 1640, 1505, 1460, 1405, 1255, 1205, 1085, 1060, 1005, 980, 895, 795, 645

NMR(DMSO-d$_6$) δ: 6.62(3H,s), 6.61(1H,s), 6.58(1H,s), 3.95(2H,t), 3.61(2H,s), 3.58(3H,s), 3.55(3H,m), 3.95(2H,t), 2.25(6H,s), 2.13(3H,s), 2.12(3H,s), 2.05(3H,s), 1.07(6H,d)

Elemental analysis (C$_{25}$H$_{37}$NO$_4$.½C$_4$H$_4$O$_4$) Calculated: C,63.14; H,$_{7.35}$; N,2.38 Found: C,62.85; H,7.36; N,2.58

Example 29

Synthesis of N-[3-hydroxy-6-(2-methoxyethoxy)-2,4,5-trimethylbenzy]-N-methyl-2-(4-hydroxy-2-isopropyl-5-methylphenoxy)ethylamine hydrochloride Triethylamine (3 ml) was added dropwise to a solution of N-methyl-2-(4-hydroxy-2-isopropyl-5-methylphenoxy) ethylamine hydrochloride (2.60 g) and 3-hydroxy-6-(2-methoxyethoxy)-2,4,5-triemthylbenzyl chloride (2.59 g) N,N-dimethylformamide (40 ml), and the mixture was stirred at room temperature for 16 hours. After the completion of the reaction, the reaction mixture was poured on ice water and extracted with ethyl acetate. The obtained extract was washed with water, dried and concentrated to give 3.2 g of a pale-brown oil. The oil was dissolved in methanol (50 ml) and conc. hydrochloric acid (2 ml) was added. The mixture was refluxed under heating for 5 hours. After cooling, the solvent was distilled off under reduced pressure, and the residue was recrystallized from water to give 3.32 g of the title compound (colorless crystals).

Melting point: 106.8°–108.8° C.

IR(KBr) cm$^{-1}$: 3480, 3200, 2970, 1625, 1520, 1460, 1410, 1265, 1240, 1210, 1110, 1095, 1070, 1030, 945, 905, 880, 825, 740, 670,

NMR(DMSO-d$_6$) δ: 9.45(1H,s), 8.81(1H,s), 8.24(1H,s), 6.70(1H,s), 6.68(1H,s), 4.53–4.30(4H,m), 3.82(4H,m), 3.62 (2H,m), 3.54(2H,m), 3.32(3H,s), 3.17(1H,s), 2.76(3H,d), 2.26(3H,s), 2.15(3H,s), 2.13(3H,s), 2.08(3H,s), 1.09(6H,dd)

Elemental analysis (C$_{26}$H$_{39}$NO$_5$.HCl. H$_2$O) Calculated: C,62.45; H,8.47; N,2.80; Cl,7.09 Found: C,62.58; H,8.45; N,2.90; Cl,7.18

Example 30

Synthesis of N-(2-ethoxy-5-hydroxy-3,4,6-trimethylbenzyl)-N-isopropyl-2-(4-hydroxy-2-isopropyl-5-methylphenoxy)ethylamine hydrochloride Triethylamine (7 ml) was added dropwise to a solution of N-isopropyl-2-(4-acetoxy-2-isopropyl-5-methylphenoxy) ethylamine (1.5 g) and 2-ethoxy-5-hydroxy-3,4,6-trimethylbenzyl chloride (5.28 g) in N,N-dimethylformamide (20 ml), and the mixture was stirred at room temperature for 16 hours. After the completion of the reaction, the reaction mixture was poured on ice water and extracted with ethyl acetate. The obtained extract was washed with water, dried and concentrated to give 1.42 g of a pale-brown oil. The oil was dissolved in methanol (50 ml) and conc. hydrochloric acid (2 ml) was added. The mixture was refluxed under heating for 5 hours. After cooling, the solvent was distilled off under reduced pressure, and the residue was recrystallized from ethanol-diethyl ether to give 1.27 g of the title compound (colorless crystals).

Melting point: 217.4°–219.2° C.

IR(KBr) cm$^{-1}$: 3450, 3200, 3150, 2970, 1605, 1510, 1460, 1410, 1380, 1260, 1205, 1185, 1075, 1025, 865, 830, 650

NMR(DMSO-d$_6$) δ: 8.78(1H,s), 8.60(1H,brs), 8.24(1H, s), 6.65(1H,s), 6.53(1H,s), 4.45(1H,m), 4.25(3H,m), 3.84–3.55(4H,m), 3.30(1H,m), 3.08(1H,m), 2.27(3H,s), 2.13(3H,s), 2.09(3H,s), 2.05(3H,s), 1.51(3H,d), 1.41(3H,d), 1.33(3H,t), 1.08(6H,d)

Elemental analysis (C$_{27}$H$_{41}$NO$_4$. HCl) Calculated: C,67.55; H,8.82; N,2.92; Cl,7.38 Found: C,67.20; H,8.83; N,3.06; Cl,7.66

Example 31

Synthesis of N-ethyl-N-(3-hydroxy-6-methoxy-2,4,5-trimethylbenzyl)-2-(4-hydroxy-2-isopropyl-5-methylphenoxy)ethylamine hydrochloride Triethylamine (5.6 ml) was added dropwise to a solution of N-ethyl-2-(4-acetoxy-2-isopropyl-5-methylphenoxy)

ethylamine (3.85 g) and 3-hydroxy-6-methoxy-2,4,5-trimethylbenzyl chloride (6.44 g) in N,N-dimethylformamide (50 ml), and the mixture was stirred at room temperature for 16 hours. After the completion of the reaction, the reaction mixture was poured on ice water and extracted with ethyl acetate. The obtained extract was washed with water, dried and concentrated to give 3.85 g of a pale-brown oil. The oil was dissolved in methanol (50 ml) and conc. hydrochloric acid (2 ml) was added. The mixture was refluxed under heating for 5 hours. After cooling, the solvent was distilled off under reduced pressure, and the residue was recrystallized from ethanol-diethyl ether to give 3.16 g of the title compound (colorless crystals).

Melting point: 208.7°–209.7° C.

IR(KBr) cm$^{-1}$: 3400, 3220, 3170, 2960, 1600, 1520, 1455, 1415, 1375, 1355, 1265, 1210, 1190, 1095, 1070, 1020, 970, 875, 840, 805, 660, 595

NMR(DMSO-d$_6$) δ: 9.24(1H,brs), 8.85(1H,brs), 8.27(1H,brs), 6.68(2H,s), 4.40(2H,d), 4.31(2H,t), 3.61(3H,s), 3.47(2H,m), 3.25(2H,m), 3.13(1H,m), 2.28(3H,s), 2.14(6H,s), 2.08(3H,s), 1.36(3H,t), 1.08(6H,m)

Elemental analysis (C$_{25}$H$_{37}$NO$_4$·HCl) Calculated: C,66.43; H,8.47; N,3.10; Cl,7.84 Found: C,66.05; H,8.66; N,3.19; Cl,8.06

Example 32

Synthesis of N-(2,5-dimethoxy-3,4,6-trimethylbenzyl)-N-methyl-2-(2-isopropyl-4-methoxy-5-methylphenoxy)ethylamine monofumarate N-(2,5-Dimethoxy-3,4,6-trimethylbenzyl)-N-methyl-2-(4-hydroxy-2-isopropyl-5-methylphenoxy)ethylamine (2.32 g), methyl iodide (0.6 ml) and benzyltrimethylammonium chloride (0.8 g) were added to a mixed solvent of a 40% sodium hydroxide aqueous solution (40 ml) and methylene chloride (80 ml), and the mixture was stirred at room temperature for 16 hours. The methylene chloride layer was partitioned, washed, dried and concentrated to give 2.1 g of a pale-brown oil. The oil was dissolved in ethanol, and fumaric acid (0.5 g) was added. The mixture was heated for dissolution. The solvent was distilled off under reduced pressure, and the residue was recrystallized from ethanol-diethyl ether to give 1.05 g of the title compound (colorless crystals).

Melting point: 126.1°–128.4° C.

IR(KBr) cm$^{-1}$: 3450, 2970, 1720, 1655, 1605, 1580, 1500, 1465, 1410, 1305, 1255, 1210, 1090, 1005, 795, 760, 645

NMR(DMSO-d$_6$) δ: 6.71(2H,s), 6.62(2H,s), 3.97(2H,t), 3.72(3H,s), 3.58(5H,s), 3.55(3H,s), 3.20(1H,m), 2.77(2H,t), 2.25(3H,s), 2.23(3H,s), 2.12(3H,s), 2.11(3H,s), 2.08(3H,s), 1.12(6H,d)

Elemental analysis (C$_{26}$H$_{39}$NO$_4$·C$_4$H$_4$O$_4$) Calculated: C,66.03; H,7.94; N,2.57 Found: C,65.81; H,7.88; N,2.84

Industrial Applicability

The compound of the present invention has a blocking effect on α-adrenoceptor, in particular, extremely potent blocking effect on α$_1$-adrenoceptor which is a subtype of the α-adrenoceptor. Accordingly, the compound of the present invention can be used for the treatment of various diseases related to the sympathetic nervous system, particularly those caused by α-adrenoceptor. Examples of such diseases include hypertension, pulmonary hypertension, congestive heart failure, myocardial ischemia, arrhythmia, angina pectoris, peripheral vascular diseases, cardiovascular disorders due to the change in vascular resistance, abnormal serum lipid, benign prostatic hypertrophy, dysuria, diabetes, glaucoma, ocular hypertension, obesity, colic convulsion, gastrointestinal dyskinesia (e.g. irritable intestinal syndromes and constipation) and central nervous diseases (e.g. impotence, depression and senile dementia).

What is claimed is:

1. A novel benzylaminoethoxybenzene derivative of the formula (I)

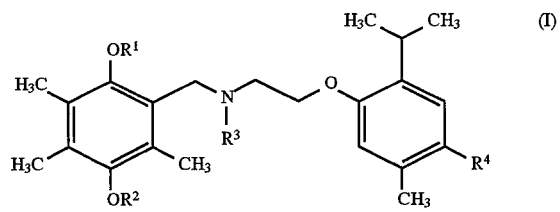

wherein

R$^1$ is a hydrogen atom, a lower alkyl, a lower hydroxyalkyl, a lower alkoxyalkyl, an allyl or a benzyl;

R$^2$ is a hydrogen atom, a lower alkyl, a lower acyl, an allyl or a benzyl;

R$^3$ is a hydrogen atom, a lower alkyl, a lower alkoxyalkyl, a lower dialkylaminoalkyl or a lower acyl; and R$^4$ is a hydrogen atom, a halogen atom, a lower alkoxy, an amino, a lower acylamino, a hydroxy, a lower acyloxy, a lower acyl, a carboxy or a lower alkoxycarbonyl, a salt thereof or a solvate thereof.

2. The benzylaminoethoxybenzene derivative of claim 1, which is expressed by the formula (I')

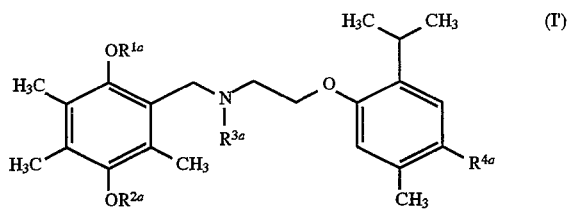

wherein

R$^{1a}$ is a hydrogen atom, a lower alkyl, a lower hydroxyalkyl or a lower alkoxyalkyl;

R$^{2a}$ is a hydrogen atom or a lower acyl;

R$^{3a}$ is a hydrogen atom, a lower alkyl or a lower alkoxyalkyl; and

R$^{4a}$ is a hydroxy or a lower acyloxy, a salt thereof or a solvate thereof.

3. The benzylaminoethoxybenzene derivative of claim 1, which is a member selected from the group consisting of N-(3-hydroxy-6-methoxy-2,4,5-trimethylbenzyl)-N-methyl-2-(4-hydroxy-2-isopropyl-5-methylphenoxy)ethylamine, N-(3-hydroxy-6-methoxy-2,4,5-trimethylbenzyl)-2-(4-hydroxy-2-isopropyl-5-methylphenoxy)ethylamine, and N-(2-ethoxy-5-hydroxy-3,4,6-trimethylbenzyl)-N-methyl-2-(4-hydroxy-2-isopropyl-5-methylphenoxy)ethylamine, a salt thereof or a solvate thereof.

4. A pharmaceutical composition comprising a benzylaminoethoxybenzene derivative of the formula (I)

27

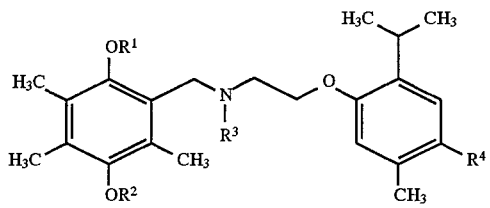
(I)

wherein R¹ is a hydrogen atom, a lower alkyl, a lower hydroxyalkyl, a lower alkoxyalkyl, an allyl or a benzyl; R² is a hydrogen atom, a lower alkyl, a lower acyl, an allyl or a benzyl; R³ is a hydrogen atom, a lower alkyl, a lower alkoxyalkyl, a lower dialkylaminoalkyl or a lower acyl; and R⁴ is a hydrogen atom, a halogen atom, a lower alkoxy, an amino, a lower acylamino, a hydroxy, a lower acyloxy, a lower acyl, a carboxy or a lower alkoxycarbonyl, a salt thereof or a solvate thereof, and a carrier.

5. The pharmaceutical composition of claim 4, wherein the benzylaminoethoxybenzene derivative is a benzylaminoethoxybenzene derivative of the formula (I')

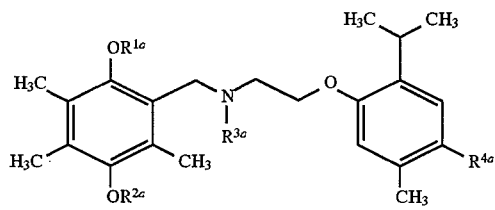
(I')

wherein R¹ᵃ is a hydrogen atom, a lower alkyl, a lower hydroxyalkyl or a lower alkoxyalkyl; R²ᵃ is a hydrogen atom or a lower acyl; R³ᵃ is a hydrogen atom, a lower alkyl or a lower alkoxyalkyl; and R⁴ᵃ is a hydroxy or a lower acyloxy, a salt thereof or a solvate thereof, and a carrier.

6. The pharmaceutical composition of claim 4, comprising a benzylaminoethoxybenzene derivative which is a member selected from the group consisting of N-(3-hydroxy-6-methoxy-2,4,5-trimethylbenzyl)-N-methyl-2-(4-hydroxy-2-isopropyl-5-methylphenoxy)ethylamine, N-(3-hydroxy-6-methoxy-2,4,5-trimethylbenzyl)-2-(4-hydroxy-2-isopropyl-5-methylphenoxy)ethylamine, and N-(2-ethoxy-5-hydroxy-3,4,6-trimethylbenzyl)-N-methyl-2-(4-hydroxy-2-isopropyl-5-methylphenoxy)ethylamine, a salt thereof or a solvate thereof, and a carrier.

7. A method for producing a benzylaminoethoxybenzene derivative of the formula (I)

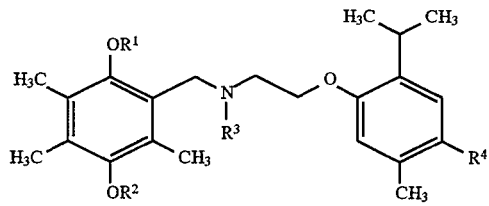
(I)

wherein R¹ is a hydrogen atom, a lower alkyl, a lower hydroxyalkyl, a lower alkoxyalkyl, an allyl or a benzyl; R² is a hydrogen atom, a lower alkyl, a lower acyl, an allyl or a benzyl; R³ is a hydrogen atom, a lowe alkyl, a lower alkoxyalkyl, a lower dialkylaminoalkyl or a lower acyl; and R⁴ is a hydrogen atom, a halogen atom, a lower alkoxy, an amino, a lower acylamino, a hydroxy, a lower acyloxy, a lower acyl, a carboxy or a lower alkoxycarbonyl, comprising condensing a benzene derivative of the formula (II)

28

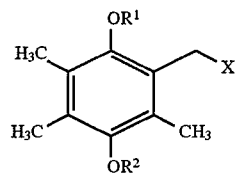
(II)

wherein R¹ and R² are as defined above, and X is a halogen atom, an alkylsulfonyloxy having 1 to 4 carbon atoms or arylsulfonyloxy having 6 to 10 carbon atoms, with an amine of the formula (III)

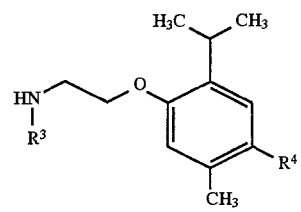
(III)

wherein R³ and R⁴ are as defined above, or an acid addition salt thereof, in a solvent or without solvent in the presence or absence of a base from under cooling to under heating (under reflux).

8. A method for producing a benzylaminoethxybenzene derivative of the formula (I)

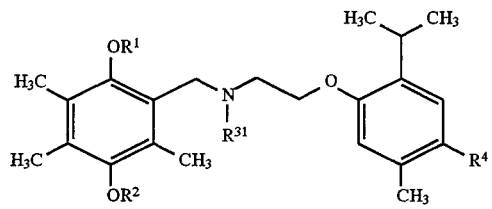
(I)

wherein R¹ is a hydrogen atom, a lower alkyl, a lower hydroxyalkyl, a lower alkoxyalkyl, an allyl or a benzyl; R² is a hydrogen atom, a lower alkyl, a lower acyl, an allyl or a benzyl; R⁴ is a hydrogen atom, a halogen atom, a lower alkoxy, an amino, a lower acylamino, a hydroxy, a lower acyloxy, a lower acyl, a carboxy or a lower alkoxycarbonyl; and R³¹ is a hydrogen atom; comprising dehydratively condensing a benzaldehyde derivative of the formula (IV)

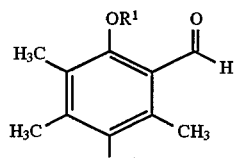
(IV)

wherein R¹ and R² are as defined above, with an amine of the formula (V)

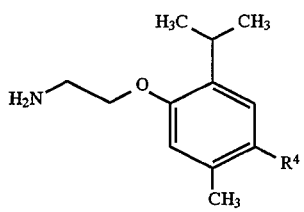
(V)

wherein R⁴ is as defined above, in a solvent or without solvent in the presence or absence of a dehydrating agent and an acid or base catalyst from under cooling to under heating (under reflux) to give a benzilidenealkylamine derivative of the formula (VI)

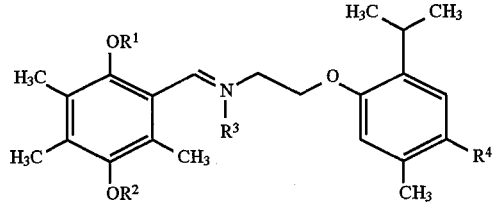 (VI)
wherein $R^1$, $R^2$ and $R^4$ are as defined above, as an intermediate for synthesis, and reducing this derivative in a solvent or without solvent using a reducing agent from under cooling to under heating (under reflux).
* * * * *

UNITED STATES PATENT AND TRADEMARK OFFICE
CERTIFICATE OF CORRECTION

PATENT NO. : 5,624,961

DATED : April 29, 1977

INVENTOR(S) : Ban et al.

It is certified that error appears in the above-identified patent and that said Letters Patent is hereby corrected as shown below:

In Column 1, line 17, "prostrate" should read --prostatic--.

In column 4, line 22, "2-( 4-acetylamino" should read --2-(4-acetylamino--.

In column 5, line 39, "las" should read --1 as--.

In column 9, line 32, "The include" should read --The carriers and excipients for manufacturing pharmaceuticals include--.

In column 13, line 43, "ethyl{" should read --ethyl}--.

In column 13, lines 57 and 58, the sentence "The solvent was distilled off under anhydrous sodium sulfate." should be deleted.

In column 18, line 58, "6.58(1H,m)" should read --6.58(1H,s)--.

In column 21, line 14, "isoprpyl" should read --isopropyl--.

UNITED STATES PATENT AND TRADEMARK OFFICE
CERTIFICATE OF CORRECTION

PATENT NO. : 5,624,961
DATED : April 29, 1977
INVENTOR(S) : Ban et al.

It is certified that error appears in the above-identified patent and that said Letters Patent is hereby corrected as shown below:

In column 21, line 32, "8.88(1H,s) should read --8.88(1H,brs)--.

In column 22, line 58, "1580, 1580" is duplicated. The second entry should be deleted.

In column 23, line 23, "3450, 1755" should read --3450, 2960, 1755--.

In column 23, lines 55 and 56, "3.55(3H,m), 3.95(2H,t), 2.25" should read --3.55(3H,s), 3.13(1H,m), 2.79(2H,t), 2.25--.

In column 23, line 58, "H,7.35" should read --H,7.35--.

In column 24, line 2, "triemthylbenzyl" should read --trimethylbenzyl--.

In column 24, line 18, "9.45(1H,s) should read --9.45(1H,brs)--.

Signed and Sealed this

Fourth Day of November, 1997

Attest:

Attesting Officer

BRUCE LEHMAN

Commissioner of Patents and Trademarks